US012653892B2

(12) United States Patent
Wender et al.

(10) Patent No.: US 12,653,892 B2
(45) Date of Patent: Jun. 16, 2026

(54) COMPOSITION AND METHOD FOR NEW THERAPEUTIC AGENTS INCLUDING GUANIDINIUM-PRESENTING DENDRIMERS AND BRANCHED STRUCTURES

(71) Applicant: The Board of Trustees of the Leland Stanford Junior University, Stanford, CA (US)

(72) Inventors: Paul Wender, Menlo Park, CA (US); Lynette Cegelski, Palo Alto, CA (US); Jasna Brcic, Redwood City, CA (US); Madeline Chosy, Redwood City, CA (US); Harrison P. Rahn, Redwood City, CA (US); Jiuzhi Sun, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 688 days.

(21) Appl. No.: 18/009,287

(22) PCT Filed: Jun. 16, 2021

(86) PCT No.: PCT/US2021/037662

§ 371 (c)(1),
(2) Date: Dec. 8, 2022

(87) PCT Pub. No.: WO2021/257723

PCT Pub. Date: Dec. 23, 2021

(65) Prior Publication Data

US 2023/0226197 A1 Jul. 20, 2023

Related U.S. Application Data

(60) Provisional application No. 63/040,967, filed on Jun. 18, 2020.

(51) Int. Cl.
*A61K 47/54* (2017.01)

(52) U.S. Cl.
CPC .................................. *A61K 47/549* (2017.08)

(58) Field of Classification Search
CPC ..... A61K 47/543; A61K 47/549; A61K 47/56
See application file for complete search history.

(56) References Cited

U.S. PATENT DOCUMENTS

| | | | | |
|---|---|---|---|---|
| 7,482,376 B2 * | 1/2009 | Subasinghe | A61P 17/06 514/438 |
| 2008/0221043 A1 * | 9/2008 | Harth | A61K 47/56 564/241 |
| 2019/0388460 A1 * | 12/2019 | Hedrick | C08G 64/0241 |
| 2020/0147227 A1 * | 5/2020 | Im | A61P 35/00 |
| 2023/0146239 A1 * | 5/2023 | Boger | A61P 31/04 514/3.1 |

OTHER PUBLICATIONS

Antonoplis et al. (2019) "A Vancomycin-Arginine Conjugate Inhibits Growth of Carbapenem resistant *E. coli* and Targets Cell-Wall Synthesis", ACS Chem Bioi. 14(9): pp. 2065-2070.

Chamorro et al. (2012) "Enhancing membrane disruption by targeting and multivalent presentation of antimicrobial peptides", Biochimica et Biophysica Acta. 1818, pp. 2171-2174, especially: abstract; p. 2173, Scheme 1, formula 4; p. 2173.

McKinlay et al. (2016) "Cell-Penetrating, Guanidinium-Rich Oligophosphoesters: Effective and Versatile Molecular Transporters for Drug and Probe Delivery", JAm Chem Soc. 138(10): pp. 3510-3517.

Jiang et al. (2021) "Recent advances in design of antimicrobial peptides and polypeptides toward clinical translation", Advanced Drug Delivery Reviews. 170, pp. 261-280.

* cited by examiner

*Primary Examiner* — Pancham Bakshi
(74) *Attorney, Agent, or Firm* — Pamela J. Sherwood; Bozicevic, Field & Francis LLP

(57) ABSTRACT

The design, synthesis, and biological evaluation of a new family of highly effective conjugate compounds, including dendrimeric moieties and branched structures, are described. Pharmaceutical compositions including the subject dendrimeric conjugates and methods of using the same are also provided. Methods of using the subject dendrimeric conjugates include delivering a cargo moiety conjugated to the dendrimeric moieties and branched structures to a cell under suitable conditions. In certain embodiments, the cell is a bacterial cell population, and the subject compounds reduce the bacterial cell population. In certain embodiments of the methods, the subject compound is capable of eradicating one or more of Gram-positive bacteria, mycobacteria, and Gram-negative bacteria. In certain embodiments of the methods, the subject compound is capable of eradicating bacterial biofilms. Methods of using the subject dendrimeric conjugates include treating a subject for a disease or condition. In certain embodiments, the disease or conditions an infectious disease.

2 Claims, 3 Drawing Sheets

COMPOSITION AND METHOD FOR NEW THERAPEUTIC AGENTS INCLUDING GUANIDINIUM-PRESENTING DENDRIMERS AND BRANCHED STRUCTURES

CROSS-REFERENCE TO RELATED APPLICATION

The present application claims the benefit of PCT Application No. PCT/US2021/037662, filed on Jun. 16, 2021, which claims priority to U.S. Provisional Patent Application No. 63/040,947 filed Jun. 18, 2020, the entire disclosure of which is hereby incorporated by reference herein in its entireties for all purposes.

BACKGROUND

Molecular transporters (MoTrs) are agents that enable or enhance the translocation of drugs or other cargo across biological barriers. A number of different cargo loads can be transported, including, for example, small molecules, imaging agents, metals, peptides, proteins, plasmids, and siRNA. Transport of larger assemblies such as quantum dots, iron particles, and vesicles has also been enhanced by transporters. Molecular transporter technology has been evaluated in conditions including overcoming multidrug resistant cancer in cellular and animal models, even when the drug alone succumbs to resistance; and overcoming antibiotic resistance.

For example, an increase in prevalence of chronic, difficult to treat and often lethal infections, coupled to a 90% decline in new antibiotic approvals over the last 30 years by the FDA, renders treatment of many bacterial infections an urgent challenge and unsolved problem. Without significant advances in antibacterial drug design, discovery and development, in the future the threat of infection could begin to outweigh the benefits of what are now considered standard surgical procedures. The rise in multi-drug resistance and exhaustion of last-resort antimicrobials also pose a specific threat to individuals undergoing chemotherapy and others affected by immune suppression. The introduction of new antimicrobials is urgently needed to address the threat of antibiotic resistance and tolerance.

Further development of molecular transporters is of great interest as a solution to the ongoing problem of developing approaches for the delivery of drugs and biologics.

SUMMARY OF THE DISCLOSURE

The design, synthesis, and biological evaluation of a family of highly effective conjugate compounds, comprising dendrimeric moieties and branched structures conjugated to a cargo moiety, are described herein.

In some embodiments pharmaceutical compositions are provided, comprising including the dendrimeric moieties and branched structures conjugated to a cargo moiety as described herein. The compositions may be formulated in combination with a pharmaceutically acceptable excipient.

In some embodiments, methods of delivering a cargo moiety to a cell under suitable conditions are provided, where the cargo moiety is conjugated to one or more dendrimeric moieties and branched structures as described herein. Methods of using the subject dendrimeric conjugates include treating a subject for a disease or condition. In certain embodiments, the disease or condition is an infectious disease. In certain embodiments the disease or conditions is cancer. In certain embodiments, the cell is a bacterial cell population, and the subject compounds reduce the bacterial cell population. In some such embodiments the cargo moiety is an antibiotic. In certain embodiments, the subject compound is capable of eradicating both Gram-positive bacteria and Gram-negative bacteria.

DETAILED DESCRIPTION

Figure 1:
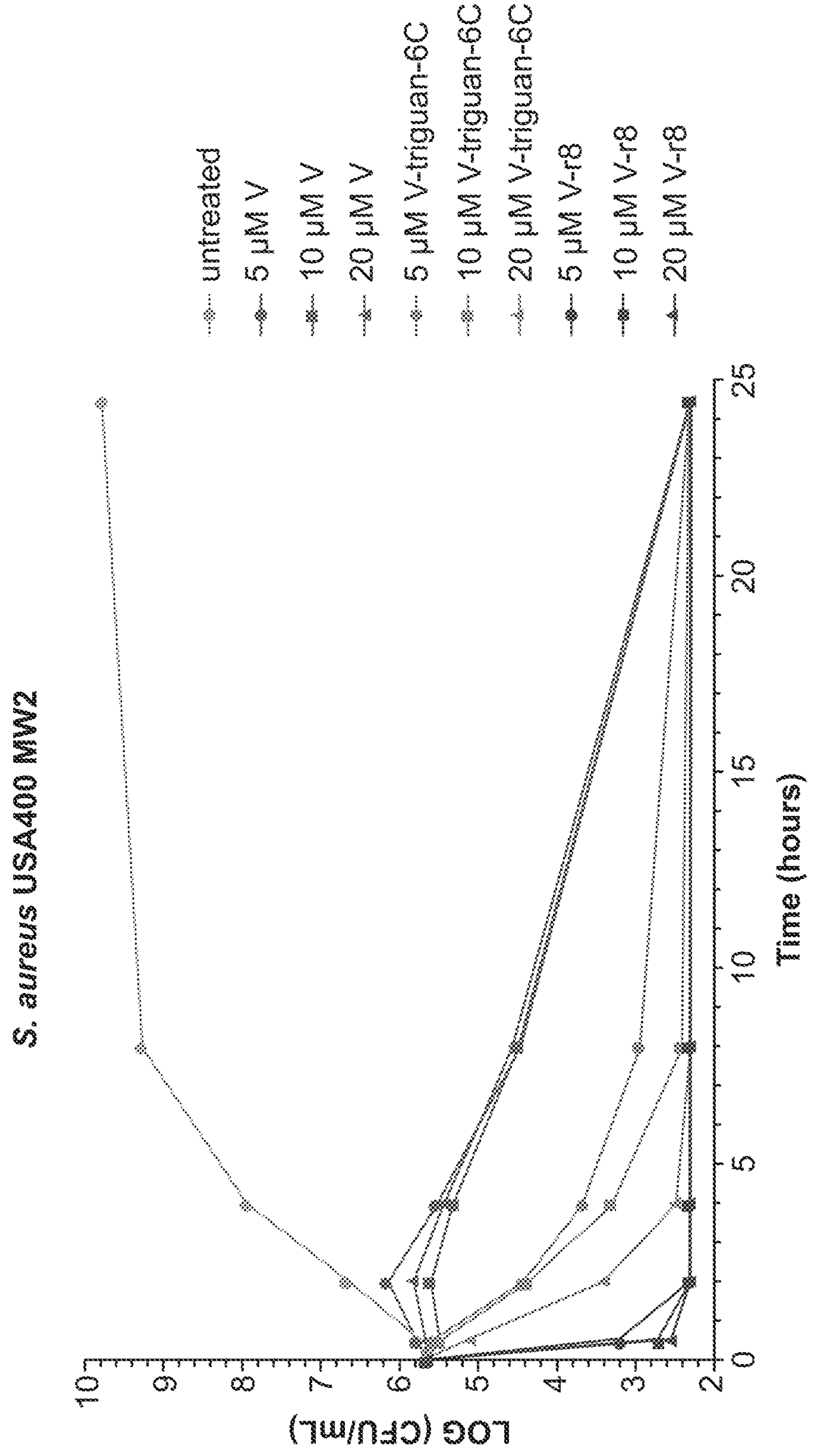
FIG. 1. Time-kill kinetics of V-triguan-6C against *S. aureus* USA400 (MRSA). V-triguan-60 kills *S. aureus* faster than vancomycin.
Figure 2:
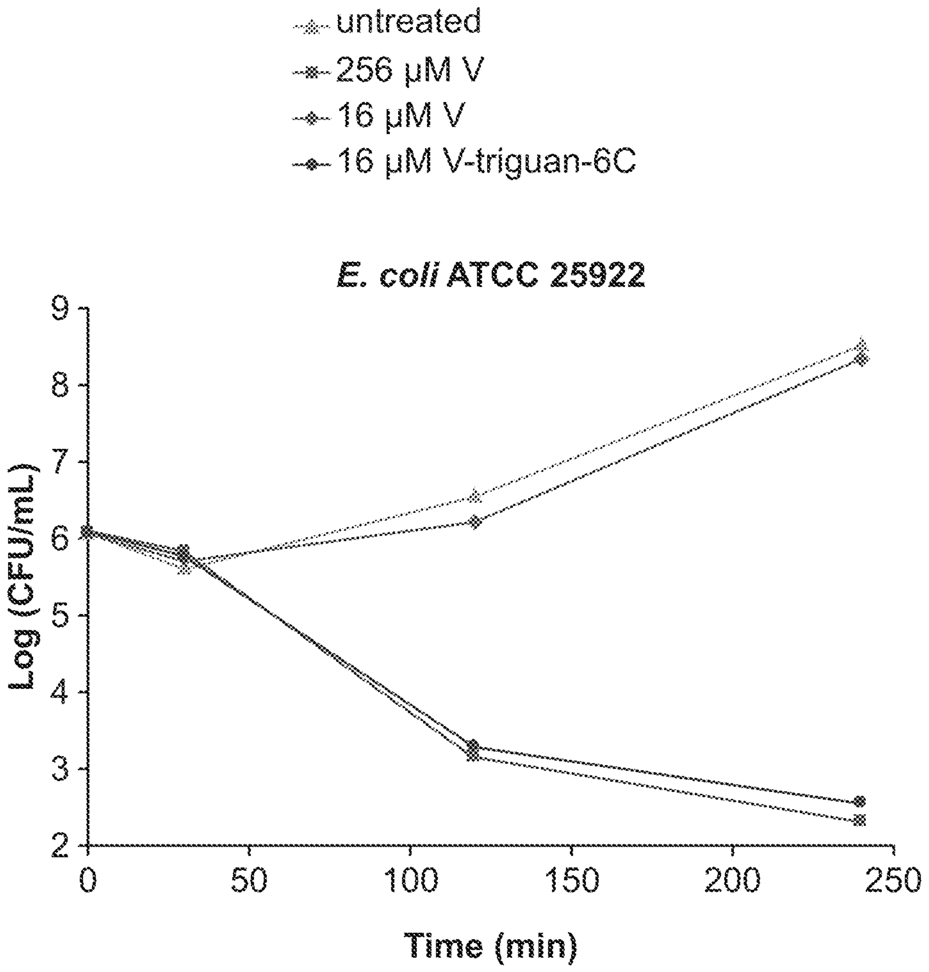
FIG. 2. Time-kill kinetics of V-triguan-6C against *E. coli* 25922. V-triguan-6C time-kill kinetics are similar to that of vancomycin, but is effective at a much lower concentration (16 μM), whereas vancomycin at 256 μM is not clinically useful.
Figure 3:
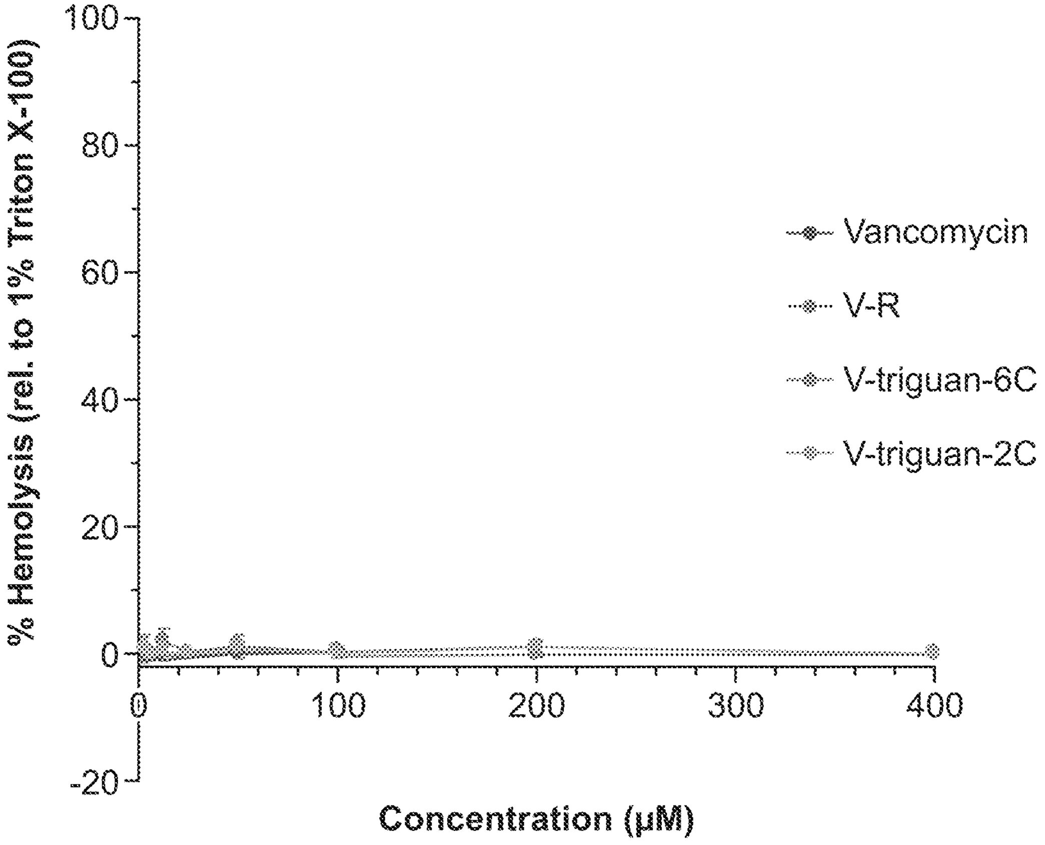
FIG. 3. Vancomycin-Dendrimer conjugates exhibit no hemolysis or toxicity.

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

As used herein, the term cargo moiety refers to any compound that is of interest for delivery to a cell. Cargo moieties of interest include, without limitation, small molecule drugs including without limitation antibiotics, antiviral agents, chemotherapeutic agents, nucleosides, polynucleotides, e.g. siRNA, mRNA, DNA, etc., proteins, fluorescent/radioactive/optical imaging agents, peptides/proteins/enzymes, nucleic acids (siRNA/RNA/DNA/etc.), metal based compounds/catalysts, polymers, site-specific cellular targeting agents (compounds/ligands/antibodies/etc.), for diverse applications such as treating infection, chemotherapeutic agents, smart adjuvants, gene therapy vectors, biosensors, bioreactors, and so forth. Any of a number of drugs are suitable for use as a cargo moiety, or can be modified to be rendered suitable for use in the subject compounds.

Cargo moieties of interest include, but are not limited to: antibiotics, e.g. antibiotics with the classes of aminoglycosides; carbapenems; and the like; penicillins, e.g. penicillin G, penicillin V, methicillin, oxacillin, carbenicillin, nafcillin, ampicillin, etc. penicillins in combination with β-lactamase inhibitors, cephalosporins, e.g. cefaclor, cefazolin, cefuroxime, moxalactam, etc; tetracyclines; cephalosporins; quinolones; lincomycins; macrolides; sulfonamides; glycopeptides including the anti-infective antibiotics vancomycin, teicoplanin, telavancin, ramoplanin and decaplanin. Derivatives of vancomycin include, for example, oritavancin and dalbavancin (both lipoglycopeptides). Telavancin is a semi-synthetic lipoglycopeptide derivative of vancomycin (approved by FDA in 2009). Other vancomycin analogs are disclosed, for example, in WO 2015022335 A1 and Chen et al. (2003) PNAS 100(10): 5658-5663, each herein specifically incorporated by reference. Non-limiting examples of antibiotics include vancomycin, linezolid, azithromycin, daptomycin, colistin, eperezolid, fusidic acid, rifampicin, tetracyclin, fidaxomicin, clindamycin, lincomycin, rifalazil, and clarithromycin.

Cargo moieties of interest include chemotherapeutic agents. Classes of chemotherapy drugs include alkylating agents; e.g. mechlorethamine, cyclophosphamide, chlorambucil, melphalan, ifosfamide; ethylenimines, eg. thiotepa, hexamethylmelamine; alkylsulfonates, e.g. busulfan; hydrazines and triazines, e.g. altretamine, procarbazine, dacarbazine, temozolomide; nitrosureas, e.g. carmustine, lomustine, streptozocin. Metal salts, e.g. carboplatin, cisplatin, oxaliplatin. Plant alkaloids include vinca alkaloids, e.g. vincristine, vinblastine, vinorelbine; taxanes, e.g. paclitaxel and docetaxel; podophyllotoxins, e.g. etoposide, tenisopide; camptothecan analogs, e.g. irinotecan, topotecan. Antitumor antibiotics include, for example, anthracyclines, e.g. doxorubicin, daunorubicin, epirubicin, mitoxantrone, idarubicin; chromomycins, e.g. dactinomycin and plicamycin; mitomycin and bleomycin. Antimetabolites include folic acid antagonist, e.g. methotrexate; pyrimidine antagonist, e.g. 5-fluorouracil, foxuridine, cytarabine, capecitabine, and gemcitabine; purine antagonist, e.g. 6-mercaptopurine and 6-thioguanine; adenosine deaminase inhibitor, e.g. cladribine, fludarabine, nelarabine and pentostatin. Topoisomerase inhibitors include topoisomerase I inhibitors, e.g. irinotecan, topotecan; topoisomerase II inhibitors, e.g. amsacrine, etoposide, etoposide phosphate, teniposide. Also included are ribonucleotide reductase inhibitor, e.g. hydroxyurea; adrenocortical steroid inhibitor, e.g. mitotane; enzymes, e.g. asparaginase and pegaspargase; antimicrotubule agent, e.g. estramustin; and retinoids, e.g. bexarotene, isotretinoin, tretinoin (atra). For example, specific cargos of interest include paclitaxel, doxorubicin, cisplatin, and bryostatin, etc. In some embodiments, the cargo moieties are anthracycline chemotherapeutic compounds, such as doxorubicin (DOX). Suitable cancer chemotherapeutic agents also include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD). Also included are allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like. Other anti-proliferative cytotoxic agents are navelbene, CPT-11, anastrazole, letrazole, capecitabine, reloxafine, cyclophosphamide, ifosamide, and droloxafine.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other suitable chemotherapeutic agents include, but are not limited to, metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include, but are not limited to, immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose). Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Cargo moieties of interest include peptides and polypeptides, such as pVI (adenovirus lytic domain), TAT (HIV lytic domain), ovalbumin, NS5A1-31 (Hep C viral membrane anchor), etc.; GFP, MOMP (*Chlamydia* protein), and EGF/EGFR, antibodies, etc.; Metals and metal ions such as Gold, Silver, Nickel and Copper (bead or catalyst), etc.; and nucleic Acids, such as DNA, RNA, and siRNA for any convenient gene of interest.

"Small molecule drug" as used herein refers to a compound, e.g., an organic compound, naturally occurring or non-naturally occurring, which exhibits a pharmaceutical activity of interest and which is generally of a molecular weight of 800 Da or less, or 2000 Da or less, but can encompass molecules of up to 5 kDa and can be as large as 10 kDa. A small inorganic molecule refers to a molecule containing no carbon atoms, while a small organic molecule refers to a compound containing at least one carbon atom. "Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule", "oligonucleotide" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), small interfering RNA (siRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

Gram-positive bacteria. Gram-positive organisms (including bacteria of the genera *Staphylococcus, Streptococcus* and *Enterococcus*) are among the most common bacterial causes of clinical infection and may be treated with the conjugates described herein. Included as organisms of interest are Staphylococci sp., Streptococci sp., Enterococci sp., *C. diptheriae, B. anthracis, C. difficile*] and specifically may include methicillin-resistant *Staphylococcus aureus* (MRSA), which is resistant to almost all b-lactam antibiotics; glycopeptide-resistant Enterococci (GRE), multidrug resistant (MDR) *Streptococcus pneumoniae*] MDR *Streptococcus agalactiae*] *Streptococcus pyogenes*] *Enterococcus faecium, Staphylococcus aureus*, multidrug-resistant *Staphylococcus epidermidis* (MRSE), etc.

The term "MRSA" as used herein refers generally to a strain of *Staphylococcus aureus* that is resistant to a large group of antibiotics called the beta-lactams, which include the penicillins and the cephalosporins. Specific examples of beta-lactam antibiotics include methicillin, dicloxacillin, nafcillin, and oxacillin. MRSA is sometimes referred to as multidrug-resistant *Staphylococcus aureus* or oxacillin-resistant *Staphylococcus aureus* (ORSA).

*Staphylococcus aureus* (*S. aureus*) is a cause of a variety of conditions in humans, including skin infections (e.g. folliculitis, styes, cellulitis, impetigo, and furunculosis), pneumonia, mastitis, phlebitis, meningitis, scalded skin syndrome, osteomyelitis, urinary tract infections, and food poisoning. Methicillin resistance is caused by the acquisition of an exogenous gene mecA that encodes penicillin-binding protein (PBP2a or PBP2'), which exhibits a low affinity for b-lactam antibiotics. The mecA gene also is found in coagulase-negative *Staphylococcus* strains that are less pathogenic than *S. aureus*. These strains include *S. epidermidis, S. haemolyticus, S. saprophyticus, S. capitis, S. warned, S. sciuri* and *S. caprae*. An additional mec gene, named mecC, was discovered which also confers beta-lactam resistance.

Vancomycin-resistant *Enterococcus* is another significant threat to public health. Six different types of vancomycin resistance are shown by *Enterococcus*: Van-A, Van-B, Van-C, Van-D, Van-E and Van-G. The mechanism of resistance to vancomycin found in *Enterococcus* involves the alteration of the peptidoglycan synthesis pathway. The D-alanyl-D-lactate variation results in the loss of one hydrogen-bonding interaction (four, as opposed to five for D-alanyl-D-alanine) being possible between vancomycin and the peptide. The D-alanyl-D-serine variation causes a six-fold loss of affinity between vancomycin and the peptide, likely due to steric hindrance.

Gram-negative bacteria. Gram-negative bacteria are characterized by their cell envelopes, which are composed of a thin peptidoglycan cell wall sandwiched between an inner cytoplasmic cell membrane and a bacterial outer membrane; and may be treated with the conjugates described herein. The Gram-negative bacteria include *Escherichia coli*, and many pathogenic bacteria, such as *Klebsiella pneumoniae, Pseudomonas aeruginosa, Neisseria gonorrhoeae, Chlamydia trachomatis, Yersinia pestis*, and *Vibrio cholerae*. They are an important medical challenge, as their outer membrane protects them from many antibiotics.

Gram-negative bacteria are intrinsically resistant to certain antibiotics, including for example vancomycin, because the outer membranes are impermeable to large glycopeptide molecules, with the exception of some non-gonococcal *Neisseria* species. Surprisingly, vancomycin conjugates described herein are effective against certain Gram-negative bacteria, including without limitation *V. cholerae*.

Mycobacteria. Treatment of *Mycobacterium* infection with the compounds disclosed herein is of interest Mycobacteria are a diverse genus, usually separated into two broad categories: tuberculosis-causing mycobacteria (*Mycobacterium tuberculosis* complex) and non-tuberculous mycobacteria (NTM). In addition, *Mycobacterium leprae*, which is genetically and phenotypically distinct from all other identified *mycobacterium* species owing to its evolutionary genome reduction, is often represented in a distinct genetic clade. Typically, NTM are highly abundant in environmental niches such as soil and natural and drinking water sources, often leading to high rates of human-pathogen contact. In addition, several host factors, such as the increasing age of the global population, lung diseases (including cystic fibrosis and bronchiectasis), immunosuppression and broad-spectrum antibiotic therapy, contribute to the rise of NTM infections, which frequently surpass the global incidence of new tuberculosis infections in developed countries.

*Mycobacterium tuberculosis* complex (MTC) species are characterized by 99.9% similarity at the nucleotide level and identical 16S rRNA sequences, but they differ widely in terms of their host tropisms, phenotypes, and pathogenicity. The MTC includes *Mycobacterium tuberculosis, Mycobacterium africanum, Mycobacterium bovis, Mycobacterium microti, Mycobacterium canettii, Mycobacterium caprae, Mycobacterium pinnipedii, Mycobacterium suricattae, Mycobacterium mungi, Mycobacterium dassie*, and *Mycobacterium oryx*. From those species, *M. tuberculosis* is the most well-known member, infecting more than one-third of world's human population; it is also able to infect animals that have contact with humans.

Lung disease is the most common clinical manifestation of NTM infection. However, NTM infections are phenotypically diverse, manifesting themselves as a large spectrum of diseases affecting nearly all organs. Among the NTM species, *Mycobacterium avium* complex (MAC), *Mycobacterium kansasii, Mycobacterium abscessus* and also in certain regions *Mycobacterium xenopi* and *Mycobacterium malmoense* are responsible for most cases of pulmonary infections. MAC and *M. abscessus* also cause systemic and/or disseminated infections. *Mycobacterium marinum* and *Mycobacterium ulcerans* are two important and truly pathogenic NTM species. These species are responsible for severe skin infections. *M. tuberculosis, M. marinum* and *M. abscessus* are the most common species responsible for skin infections, and *Mycobacterium chimaera* and *M. abscessus* are the most common species responsible for infections involving soft tissues. There is an increased incidence of *M. abscessus* infections in patients with cystic fibrosis.

Biofilm. A biofilm is an accumulation of microorganisms (bacteria, fungi, and/or protozoa, with associated bacteriophages and other viruses) embedded in a polysaccharide matrix and adherent to solid biological or non-biotic surfaces; and are suitable for treatment with the conjugates described herein. Biofilms are medically important, accounting for over 80 percent of hospital-acquired microbial infections in the body. Examples include infections of the oral soft tissues, teeth and dental implants; middle ear; gastrointestinal tract; urogenital tract; airway/lung tissue; eye; urinary tract prostheses; peritoneal membrane and peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses, internal fixation devices, percutaneous sutures; and tracheal and ventilator tubing. The microorganisms tend to be far more resistant to antimicrobial agents and to be particularly difficult for the host immune system to render an appropriate response.

A biofilm is an assemblage of microbial cells that is closely associated with a surface and enclosed in a matrix of material, including polysaccharides, DNA, and proteins. Noncellular materials such as mineral crystals, corrosion particles, clay or silt particles, or blood components, depending on the environment in which the biofilm has developed, may also be found in the biofilm matrix. Biofilm-associated organisms also differ from their planktonic (freely suspended) counterparts with respect to the genes that are transcribed. Biofilms may form on a wide variety of surfaces, including living tissues, indwelling medical devices, industrial or potable water system piping, or natural aquatic systems.

The solid-liquid interface between a surface and an aqueous medium provides an ideal environment for the attachment and growth of microorganisms. The solid surface may have several characteristics that are important in the attachment process. The extent of microbial colonization appears to increase as the surface roughness increases. This is because shear forces are diminished, and surface area is higher on rougher surfaces. The physicochemical properties of the surface may also exert a strong influence on the rate and extent of attachment. Microorganisms attach more rapidly to hydrophobic, nonpolar surfaces such as Teflon and other plastics than to hydrophilic materials such as glass or metals.

Other characteristics of the aqueous medium, such as pH, nutrient levels, ionic strength, and temperature, may play a role in the rate of microbial attachment to a substratum. Several studies have shown a seasonal effect on bacterial attachment and biofilm formation in different aqueous systems. This effect may be due to water temperature or to other unmeasured, seasonally affected parameters.

Other cell surface properties may also facilitate attachment. Several studies have shown that treatment of adsorbed cells with proteolytic enzymes caused a marked release of attached bacteria, providing evidence for the role of proteins in attachment. The O antigen component of lipopolysaccharide (LPS) has also been shown to confer hydrophilic properties to Gram-negative bacteria.

Persisters are dormant variants of regular cells that form stochastically in microbial populations and are highly tolerant to antibiotics. Persisters may be the main culprit responsible for the recalcitrance of chronic infectious disease to antimicrobial therapy. Persister cells usually comprise about 1% of the populations in the stationary-phase growth state and in biofilms.

Minimum inhibitory concentrations (MICs) are defined as the lowest concentration of an antimicrobial that will inhibit the visible growth of a microorganism after overnight incubation, and minimum bactericidal concentrations (MBCs) as the lowest concentration of antimicrobial that will prevent the growth of an organism after subculture on to antibiotic-free media. For example, see Andrews (2001) J Antimicrob Chemother. 48 Suppl 1:5-16'. Minimal biofilm eradication concentration (MBEC) is defined as the lowest concentration of an antimicrobial agent required to eradicate a biofilm.

Cancers of interest for treatment with conjugates described herein include without limitation, carcinomas, e.g. colon, prostate, breast, melanoma, ductal, endometrial, stomach, dysplastic oral mucosa, invasive oral cancer, non-small cell lung carcinoma, transitional and squamous cell urinary carcinoma, etc.; neurological malignancies, e.g. neuroblastoma, gliomas, etc.; hematological malignancies, e.g. childhood acute leukemia, non-Hodgkin's lymphomas, and other myeloproliferative disorders, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like. Cancers of interest particularly include hematologic cancers, e.g. acute myelogenous leukemia, chronic myelogenous leukemia, acute lymphocytic leukemia, Hodgkin's lymphoma, non-Hodgkin's lymphoma, multiple myeloma, etc.; ovarian cancer; breast cancer; neuroblastoma; soft tissue sarcomas; renal cell carcinoma, all of which are have a high tendency to develop multidrug resistance.

Multidrug resistant cancer. As used herein, the term "multidrug resistant", or "MDR" cancer refers to cancer cells that intrinsically or by acquired means are resistant to multiple classes of chemotherapeutic agents. A number of tumors overexpress the MDR-1 gene; including neuroblastoma, rhabdomyosarcoma, myeloma, non-Hodgkin's lymphomas, colon carcinoma, ovarian, breast carcinoma and renal cell cancer. Several tumor types with high MDR-1 expression derive from tissues that have a high expression of the gene, e.g. colonic epithelium. As a non-limiting example, such cells may be resistant to the spectrum of agents including: paclitaxel, doxorubicin, daunorubicin, mitoxantrone, actinomycin D, plicamycin, vincristine, vinblastine, colchicine, etoposide, teniposide, camptothecin and derivatives of thereof. By resistant, it is intended that the $IC_{50}$ (the half maximal (50%) inhibitory concentration) of the drug with respect to the cell is increased at least about 5-fold, a least about 10-fold, at least about 20-fold, or more relative to a non-resistant cell from the same type of cancer.

In some embodiments, the MDR cancer cells express one or more ABC transporter proteins. Mechanisms of MDR include transporter-mediated resistance conferred by increased expression of the transmembrane glycoprotein, P-glycoprotein (Pgp), the product of the MDR1 gene and a related membrane glycoprotein, the multidrug resistance protein (MRP1). The mrp1 gene encodes a 190-kilodalton (kDa) transmembrane protein, whose structure is strikingly homologous to P-glycoprotein/MDR1 and other members of the ATP-binding cassette (ABC) transmembrane transporter proteins. There are at least five other human MRP isoforms identified. Among them, MRP2 (cMOAT) and MRP3 are also capable of supporting efflux detoxification of cancer drugs, including epipodophyllotoxins (MRP2 and 3), doxorubicin, and cisplatin (MRP2). MRP1, MRP2, MRP3 and MRP4 can all act as methotrexate efflux pumps and can confer resistance to methotrexate. Expression of these transporters can confer resistance to an overlapping array of structurally and functionally unrelated chemotherapeutic agents, toxic xenobiotics and natural product drugs. Cells in culture exhibiting MDR generally show reduced net drug accumulation and altered intracellular drug distribution. The sequence of P-glycoprotein may be obtained as Genbank accession number NM_000927 (Chen et al. (1986) Cell 47:381-389.

It will be understood by one of skill in the art that P-glycoprotein-associated MDR displays significant phenotypic heterogeneity. The relative degree of cross-resistance to drugs varies based on the cell line and the selecting drug. While the level of drug resistance is roughly correlated with the level of P-glycoprotein expression, protein and RNA levels may be disproportionately higher or lower than expected for the level of resistance observed. This phenotypic diversity may be the result of both MDR1 mutations and of posttranslational modifications of the MDR1 gene product.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group (i.e., a mono-radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(═O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" refers to an alkyl group as defined herein wherein one or more carbon atoms in the alkyl chain have been optionally replaced with a heteroatom such as —O—, —N—, —S—, —$S(O)_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —$NR^aR^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, may contain 1 to 3 carbon atoms, and as a further example, such substituents may contain 1 or 2 carbon atoms (i.e., methoxy and ethoxy).

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—$CH_2$—), ethylene (—$CH_2CH_2$—), propylene (—$CH_2CH_2CH_2$—), 2-methylpropylene (—$CH_2$—$CH(CH_3)$—$CH_2$—), hexylene (—$(CH_2)_6$—) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

By the term "functional groups" is meant chemical groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO—)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-substituted $C_1$-$C_{24}$ alkylcarbamoyl (—CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—$N^+$≡$C^-$), cyanato (—O—C≡N), isocyanato (—O—$N^+$≡C—), isothiocyanato (—S—C≡N), azido (—N═$N^+$═$N^-$), formyl (—O—(CO)—H), thioformyl (—(CS)—H), amino (—$NH_2$), mono- and di-(C1-C24 alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR═NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR═N(alkyl), where R=hydrogen, alkyl, aryl, alkaryl, etc.), arylimino (—CR═N(aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SOC_2$-aryl), phosphono (—P(O)($OH)_2$), phosphonato (—P(O)(O—)$_2$), phosphinato (—P(O)(O—)), phospho (—$PO_2$), and phosphino (—$PH_2$), mono- and di-($C_1$-$C_{24}$ alkyl)-substituted phosphino, mono- and di-($C_5$-$C_{20}$ aryl)-substituted phosphine. In addition, the aforementioned functional groups may, if a particular group permits, be further substituted with one or more additional functional groups or with one or more hydrocarbyl moieties such as those specifically enumerated above.

In addition to the groups disclosed with respect to the individual terms herein, substituent groups for substituting for one or more hydrogens (any two hydrogens on a single carbon can be replaced with ═O, ═$NR^{70}$, ═N—$OR^{70}$, ═$N_2$ or ═S) on saturated carbon atoms in the specified group or radical are, unless otherwise specified, —$R^{60}$, halo, ═O, —$OR^{70}$, —$SR^{70}$, —$NR^{80}R^{80}$, trihalomethyl, —CN, —OCN, —SCN, —NO, —$NO_2$, ═$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —P(O)($O^-$)$_2$($M^+$)$_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —C(O)$O^-M^+$, —C(O)$OR^{70}$, —C(S)$OR^{70}$, —C(O)$NR^{80}R^{80}$, —C($NR^{70}$)$NR^{80}R^{80}$, —OC(O)$R^{70}$, —C(S)$R^{70}$, —OC(O) $O^-M^+$, —OC(O)$OR^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_{30}^-M^+$, —$SO_3R^{70}$, —$OSO_2R^{70}$, —$OSO_3^-M^+$, —$OSO_3R^{70}$, —$PO_3^{-2}$($M^+$)$_2$, —P(O)($OR^{70}$)$O^-M^+$, —P(O)($OR^{70}$)$_2$, ÷C(O)$R^{70}$, —C(S)$R^{70}$, —C($NR^{70}$)$R^{70}$, —$CO_2^-M^+$, —$CO_2R^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —$OCO_2^-M^+$, —$OCO_2R^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$), —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, $—O^-M^+$, $—OR^{70}$, $—SR^{70}$, $—S^-M^+$, $—NR^{80}R^{80}$, trihalomethyl, $—CF_3$, —CN, —NO, $—NO_2$, $—S(O)_2R^{70}$, $—S(O)_2O^-M^+$, $—S(O)_2OR^{70}$, $—OS(O)_2R^{70}$, $—OS(O)_2O^-M^+$, $—OS(O)_2OR^{70}$, $—P(O)(O^-)_2(M^+)_2$, $—P(O)(OR^{70})O^+M^+$, $—P(O)(OR^{70})(OR^{70})$, $—C(O)R^{70}$, $—C(S) R^{70}$, $—C(NR^{70})R^{70}$, $—C(O)OR^{70}$, $—C(S)OR^{70}$, $—C(O)NR^{80}R^{80}$, $—C(NR^{70})NR^{80}R^{80}$, $—OC(O)R^{70}$, $—OC(S) R^{70}$, $—OC(O)OR^{70}$, $—OC(S)OR^{70}$, $—NR^{70}C(O)R^{70}$, $—NR^{70}C(S)R^{70}$, $—NR^{70}C(O)OR^{70}$, $—NR^{70}C(S)OR^{70}$, $—NR^{70}C(O)NR^{80}R^{80}$, $—NR^{70}C(NR^{70})R^{70}$ and $—NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

By "linking" or "linker" as in "linking group," "linker moiety," etc., is meant a bivalent moiety that connects two groups via covalent or non-covalent bonds. As used herein, the term "linker" or "linkage" refers to a linking moiety that connects two groups and has a backbone of 200 atoms or less in length. A linker or linkage may be a covalent bond that connects two groups or a chain of between 1 and 200 atoms in length, for example of about 1, 2, 3, 4, 5, 6, 8, 10, 12, 14, 16, 18 or 20 atoms in length, such as a linker of 10 or more atoms in length, 20 atoms or more, 30 atoms or more, 40 atoms or more, 50 atoms or more in length, 100 atoms or more in length. The linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol), PEG or modified PEG linkers, peptidic linkers, ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

The cargo can be linked to the guanidinium-rich oligophosphoester according to a number of embodiments. The cargo is generally not attached to any of the guanidinium sidechains so that they are free to interact with the target membrane. The conjugates of the invention can be prepared by straightforward synthetic schemes. Furthermore, the conjugate products are usually substantially homogeneous in length and composition, so that they provide greater consistency and reproducibility in their effects than heterogeneous mixtures.

To help minimize side-reactions, guanidinium moieties can be blocked using conventional protecting groups, such as carbobenzyloxy groups (CBZ), di-t-BOC, PMC, Pbf, $N—NO_2$, and the like.

Coupling reactions are performed by known coupling methods in any of an array of solvents, such as N,N-dimethyl formamide (DMF), N-methyl pyrrolidinone, dichloromethane, water, and the like. Exemplary coupling reagents include, for example, O-benzotriazolyloxy tetramethyluronium hexafluorophosphate (HATU), dicyclohexyl carbodiimide, bromo-tris(pyrrolidino) phosphonium bromide (PyBroP), etc. Other reagents can be included, such as N,N-dimethylamino pyridine (DMAP), 4-pyrrolidino pyridine, N-hydroxy succinimide, N-hydroxy benzotriazole, and the like.

The cargo moiety may be attached to the dendrimeric moiety using a linkage that is specifically cleavable or releasable. The use of such linkages is particularly important for therapeutic drugs that are inactive until the attached transporter moiety is released. In some cases, such conjugates can be referred to as prodrugs, in that the release of the dendrimeric or branched moiety from the cargo moiety-drug results in conversion of the drug from an inactive to an active form. As used herein, "cleaved" or "cleavage" of a conjugate or linker refers to release of a therapeutic drugs from a dendrimeric or branched moiety, thereby releasing an active therapeutic drugs. "Specifically cleavable" or "specifically releasable" refers to the linkage between the dendrimeric or branched moiety and the drug being cleaved, rather than the dendrimeric or branched moiety being degraded (e.g., by proteolytic degradation). However, this "degradable" mechanism of cargo release could also be used in the invention.

In some embodiments, the linkage is a readily cleavable linkage, meaning that it is susceptible to cleavage under conditions found in vivo. Thus, upon passing into a cell the cargo is released from the dendrimeric or branched moiety. Readily cleavable linkages can be, for example, linkages that are cleaved by an enzyme having a specific activity (e.g., an esterase, protease, phosphatase, peptidase, and the like) or by hydrolysis. For this purpose, linkers containing carboxylic acid esters and disulfide bonds are sometimes preferred, where the former groups are hydrolyzed enzymatically or chemically, and the latter are severed by disulfide exchange, e.g., in the presence of glutathione. In some embodiments, the linkage is a non-covalent association in which the dendrimeric or branched moiety and cargo moiety are held together by one or more weak associations including electrostatic, hydrogen bonding, or dispersion forces.

Examples of such linking groups include alkylene, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (epithio (—S—), epidioxy (—O—O—), carbonyldioxy (—O—CO—O—), alkyldioxy (—O—$(CH_2)$n-O—), epoxyimino (—O—NH—), epimino (—NH—), carbonyl (—CO—), etc. Any convenient orientation and/or connections of the linkers to the linked groups may be used. In certain embodiments, the linker (L) includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Linkers of interest include, but are not limited to, units of polymers such as polyethylene glycols, polyethylenes and polyacrylates, amino acid residue (s), carbohydrate-based polymers or carbohydrate residues and derivatives thereof, polynucleotides, alkyl groups, aryl groups, heterocycle groups, cleavable linker groups, combinations thereof, and substituted versions thereof.

When the term "substituted" appears prior to a list of possible substituted groups, it is intended that the term apply to every member of that group. For example, the phrase "substituted alkyl and aryl" is to be interpreted as "substituted alkyl and substituted aryl."

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include 1H, 2H (i.e., D) and 3H (i.e., T), and reference to C is meant to include 12C and all isotopes of carbon (such as 13C).

Definitions of other terms and concepts appear throughout the detailed description below.

UTILITIES

In one embodiments, the guanidinium-terminated branched and dendrimeric moieties when conjugated to vancomycin, transform the antibiotic into one that is able to eradicate Gram-positive vancomycin-resistant *E. faeccuyn* (VRE), and Gram-negative bacteria. Vancomycin is known to generally be ineffective against Gram-negative bacteria and unable to breach the outer membrane and reach cell-wall targets at concentrations that are practically relevant. Remarkably, the vancomycin guanidinium-terminated branched and dendrimeric conjugates disclosed here are effective against Gram-negative bacteria, including *E. coli* and *P. aeruginosa*. Thus, the molecular presentation of guanidinium groups through branched and dendrimeric scaffolds to a parent antibiotic provides a new antimicrobial agent effective against both vancomycin-resistant Gram-positive bacteria and against Gram-negative bacteria.

Conjugates derived from variations of the design and synthetic strategy described herein have widespread potential to treat infectious diseases. These include infections already treated with vancomycin, including those caused by Gram-positive bacteria and mycobacteria, as well as infections caused by Gram-negative bacteria. Gram-negative organisms of interest include, but are not limited to *Enterobacter* species (e.g., carbapenem-resistant *Enterobacteriaceae*), *Klebsiella, pneumoniae, Acinetobacter baumanni*, and *Pseudomonas aeruginosa*. Additional organisms of interest include, *Clostridioides difficile*, and other drug-resistant *Neisseria gonorrhoeae*.

While the conjugates above are described with respect to antibiotic guanidinium-terminated dendrimeric conjugates, the compositions find use in a variety of therapeutic applications. The inventive conjugates can be effective for delivering bioactive therapeutic agents that would normally not possess the physical properties necessary to penetrate cells. This expands the chemical space available as "druggable molecules" and provides development of new diverse targets. Additionally, this delivery technology can be used to increase the efficacy of existing therapies, for example through the delivery of chemotherapeutic drug conjugates directly to cancer cells; or the delivery of antiviral drugs conjugates directly to viral cells. The addition of a subject dendrimeric or branched moiety to therapeutic molecules can additionally improve formulation properties hydrophobic drug molecules, meaning that highly nonpolar molecules can be administered in much less time, and much smaller volumes than existing treatments.

Diagnostic Imaging: The subject conjugates provide for delivery of imaging agents into cells. By attaching an imaging probe (fluorescent, bioluminescent, magnetic, PET agent, etc.) as the cargo molecule, conjugates can be used for molecular imaging, enabling localization of a reporter molecule inside of cells. By combining this technology with numerous available targeting strategies, specific cell or tissue types can be imaged, allowing for identification of cancerous areas, or detection of foreign cells such as bacteria or parasites.

Visualization of surgical procedures: Administration of fluorescent transporters that can be activated in tumor tissues can be used as a visualization tool during surgical procedures. Fluorescent tagging of tumor cells provides and simplifies resection of tumor margins and increases efficacy of surgical procedures.

Treatment of resistant disease: Guanidinium-rich dendrimeric moieties, including cargo moieties have been shown to restore the efficacy of resistance-prone drugs, such as vancomycin (e.g., as discussed above). By appending a resistant prone drug to guanidinium-rich dendrimeric moieties using a cleavable linker (e.g., a releasable disulfide linkage), the mechanism of cellular entry is altered such that the drug is no longer a substrate for drug efflux pumps, which are a major cause of drug resistance. Guanidinium-rich dendrimer moieties of resistance-prone drugs can be, for example, effective against engineered drug-resistant cell lines and maintain cytotoxicity even when the free drug (e.g., the unconjugated drug) is no longer effective.

Additional Applications: Targeting the subject conjugates to tumors, organs, or tissues using external or enzymatic activation. Formulation as a cationic gene carrier for oligonucleotides including plasmid DNA, mRNA, and siRNA. Penetration of new barriers including the blood brain barrier, algal cell wall, bacterial cell membrane and/or cell wall, skin, etc.

Slow Release from Drug Depots: These conjugates can be used for the design of biodegradable materials for the slow release of biologically active molecules from drug depots or implants.

Localized Treatment: The subject conjugates can be designed to rapidly adhere to tissues, so they can be used to retain drugs near the site of administration. By appending a drug molecule to the dendrimeric moieties and injecting in a target area, the drug may afford fewer off-target affects associated with diffusion of the drug away from the injection site.

Decorating of Nanoparticles for Increased Uptake: Functionalization of macromolecular nano- or microparticles (e.g. micelles, liposomes, protein vaults, metallic nanoparticles, quantum dots, or virus capsids) with the dendrimeric compounds can increase their uptake, allowing these other structures to reach their intracellular targets more efficiently.

Activity of Subject Conjugates: In some designed cases, the dendrimeric moieties of certain lengths and functionalities can have inherent biological activity, such as antibacterial properties. These molecules can be used as cell-penetrating therapeutics as such, or in combination therapy with an attached cargo.

These and other advantages, and features of the disclosure will become apparent to those persons skilled in the art upon reading the details of the compositions and methods of use more fully described below.

Conjugate Compositions

The design, synthesis, and biological evaluation of a new family of highly effective conjugate compounds including dendrimeric moieties and branched structures, are described.

Aspects of the disclosure include conjugate compounds including dendrimeric moieties and branched structures. Dendrimeric structures of the invention contain a branching point enabling any number of dendritic generations. In the dendrimers, a cargo moiety is functionalized at the center of the branched system or at its outer periphery. In either case, the increase in branching points results in an increase in the number of molecular generations that increase the dendrimer diameter and globular shape. Compounds of the invention may comprise a single branching point or a plurality of such branching points, providing dendrimers having one or more generations (e.g., two, three, four or more generations).

In certain embodiments, the dendrimeric or branched moiety includes one or more terminal guanidinium groups, wherein the guanidinium groups may be bonded to a dendron branch point via a linker (e.g., as described herein). In certain cases the dendron branch point includes one or more successive generations of linkages terminating in one or more guanidine groups. The dendron branch point can be conjugated to a cargo moiety, optionally through an additional linker.

The dendrimeric moieties may be joined either covalently or non-covalently to a cargo moiety of interest, including without limitation small molecule drugs including without limitation antibiotic agents, chemotherapeutic agents, peptides, nucleosides, polynucleotides, proteins, siRNA, mRNA, plasmids, metals, imaging agents, sensors and the like. In some designed cases, dendrimeric conjugate compounds of certain lengths and functionalities have been demonstrated to have inherent biological activity, so these molecules can be used as cell-penetrating therapeutics, or in combination therapy with an attached cargo moiety.

In some embodiments there is provided a compound of formula (I):

$$Z^1\text{-}(L^1\text{-}X^1\text{-}J^1\text{-}(L^2\text{-}Z^2)_n)_m \qquad (I)$$

wherein:

$Z_1$ is a cargo moiety;

$L_1$ is an optional linker;

$X^1$ is a conjugation point;

$J^1$ is a dendron branch point;

$L^2$ is a linker;

$Z^2$ is a pendant moiety comprising a terminal group selected from a guanidine group, a protected guanidine group, and an oligophosphotriester; or $Z^2$ is $-J^1(L^2-Z^2)n$;

n is 2 or 3; and m is an integer from 1 to 20.

In some instances of formula (I), the linker $L^2$ is a C1-C20 linker, such as an substituted or unsubstituted C1-C20 alkyl linker or a C2-C20 linker comprising one or more double or triple bonds. In some cases, $L^2$ is a non-cleavable linker, e.g., a non-cleavable linker as described herein. In some embodiments of formula (I), $L^2$ is $—(CH_2)_{nx}—$, where nx is 1 to 20, such as 2 to 10, such as 2, 3, 4, 5, 6, 7, 8, 9 or 10. In some cases one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. In some embodiments, the carbon chain is interrupted by one or more atoms selected from sulfur, nitrogen or oxygen.

In some instances of formula (I), each pendant moiety $Z^2$ is a guanidine group. The guanidine groups of the subject compounds can be protected or masked (e.g., during synthesis) and then deprotected or unmasked according to any convenient strategy. In some embodiments of formula (I), $Z^2$ is an guanidine group (e.g., $—NHC(=NH)—NH_2$ or $—NHC(=NH_{2+})—NH_2$). It is understood that the guanidine group can be charged or uncharged depending on the local environment, e.g., physiological aqueous conditions around or inside a cell. In some embodiments of formula (I), $Z^2$ is a protected guanidine group (e.g., $—NHC(=NX_a)—NHX_a$, where each $X_a$ is a guanidine protecting group, such as a Boc protecting group.

In some other embodiments of formula (I), $Z^2$ is a point of branching enabling a successive generation of $-J^1(L^2-Z^2)n$. In such cases, $Z^2$ is $-J^1(L^2-Z^2)n$, having the structure $$Z^1\text{-}(L^1\text{-}X^1\text{-}J^1\text{-}(L^2\text{-}J^1(L^2\text{-}Z^2)_a)_n)_m \qquad (Ia)$$

wherein each of $Z^1$, $L^1$, $X^1$, $J^1$, $L^2$, $Z^2$, n and m are as defined above and wherein a is 2 or 3.

Accordingly, a successive generation includes a second branch point ($J^1$), a second linker (e.g., $L^2$, as described herein), and terminates in a pendant moiety $Z^2$ as described above. Or alternatively, $Z^2$ is another successive generation of $-J^1(L^2-Z^2)n$. Successive generations of the dendrimeric moiety can be produced by building up the dendrimer layers in succession, one after another according to the reaction conditions provided herein.

In certain embodiments of formula (I), the compound is of the formula (II):

$$Z^1\text{-}(L^1\text{-}X^1\text{-}J^1\text{-}(L^3\text{-}X^2\text{-}L^4\text{-}Z^3)_n)_m \qquad (II)$$

wherein:

$Z_1$ is a cargo moiety;

$L_1$ is an optional linker;

$X^1$-$X^2$ are each conjugation points;

$J^1$ is a dendron branch point;

$L^3$ is a linker;

$L^4$ is a linker comprising 2-10 atoms, wherein the linker optionally comprises one or more additional branching points;

$Z^3$ is a terminal group selected from a guanidine group, a protected guanidine group;

or $L^4$ together with $Z^3$ is $-J^1(L^3-X^2-L^4-Z^3)n$;

n is 2 or 3; and m is an integer from 1 to 20.

In some instances of formula (II), the linker $L^3$ is a C1-C20 linker, such as an substituted or unsubstituted C1-C20 alkyl linker or a C2-C20 linker comprising one or more double or triple bonds. In some cases, $L^3$ is a non-cleavable linker, e.g., a non-cleavable linker as described herein. In some embodiments of formula (I), $L^3$ is $-(CH_2)_{nx}-$, where nx is 1 to 20, such as 2 to 10, such as 2, 3, 4, 5, 6, 7, 8, 9 or 10. In some cases one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. In some embodiments, the carbon chain is interrupted by one or more atoms selected from sulfur, nitrogen or oxygen.

In certain embodiments of formula (II), $L^4$ is a C1-C20 linker, such as an substituted or unsubstituted C1-C20 alkyl linker. In some cases, $L^4$ is a non-cleavable linker, e.g., a non-cleavable linker as described herein. In some embodiments of formula (II), $L^4$ is $-(CH_2)_{nx}-$, where nx is 1 to 20, such as 2 to 10, such as 2, 3, 4, 5, 6, 7, 8, 9 or 10. In some cases one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. In certain embodiments of formula (II), $L^4$ is selected from $-(CH_2)_{nx}-$, and $-OC(O)CH(NR^3)(CH_2)_{nx})-$, wherein each $R^3$ is independently selected from H, alkyl, substituted alkyl, or a branching point, and nx is 1 to 20, such as 2 to 10, such as 2, 3, 4, 5, 6, 7, 8, 9 or 10. In some cases, L4 is $-OC(O)CH(NR^3)(CH_2)_{nx})-$, where $R^3$ is H and nx is an integer from 2 to 10. In some cases, nx is less than 10, such as 9, 8, 7, 6, 5, 4, 3 or 2. In certain cases, nx is from 2 to 6. In certain cases, nx is 6. In certain cases, nx is 5. In certain cases, nx is 4. In certain cases, nx is 3. In certain cases, nx is 3. In certain cases, nx is 2.

In certain embodiments of formula (II), $L^4$ and $Z^3$ together comprise an amino acid residue selected from lysine and arginine, wherein the C-terminus is conjugated to $X^2$. In certain cases, the amino residue is lysine. In certain cases, the amino residue is D-lysine. In certain cases, the amino residue is L-lysine. In certain cases, the amino acid is arginine. In certain cases, the amino acid is D-arginine. In certain cases, the amino acid is L-arginine. In certain cases, $L^4$ and $Z^3$ together form a branched derivative of lysine or arginine. In some cases, the branched derivative of lysine or arginine is branched through the amine group alpha to the C-terminus. In certain cases, the branched arginine or lysine derivative comprises one or more additional amino acids. In certain cases, the branched arginine or lysine derivative comprises one or more guanidine groups. In certain cases, the branched arginine or lysine derivatives include one or more successive generations of $-J^1(L^2-Z^2)n$ (e.g., as described herein).

In some instances of formula (II), each pendant moiety $Z^3$ is a guanidine group. The guanidine groups of the subject compounds can be protected or masked (e.g., during synthesis) and then deprotected or unmasked according to any convenient strategy. In some embodiments of formula (II), $Z^3$ is an guanidine group (e.g., $-NHC(=NH)-NH_2$ or $-NHC(=NH_{2+})-NH_2$). It is understood that the guanidine group can be charged or uncharged depending on the local environment, e.g., physiological aqueous conditions around or inside a cell. In some embodiments of formula (II), $Z^3$ is a protected guanidine group (e.g., $-NHC(=NX_a)-NHX_a$, where each $X_a$ is a guanidine protecting group, such as a Boc protecting group.

In some other embodiments of formula (II), $Z^3$ is a point of branching enabling successive generation of $-J^1(L^3-X^2-L^4-Z^3)n$. Accordingly, a successive generation includes a second branch point ($J^1$), second linkers (e.g., $L^3$, and $L^4$, as described herein), a second $X^2$ group, and terminates in a pendant moiety $Z^3$ as described above. Or alternatively, $Z^3$ is another successive generation of $-J^1(L^3-X^2-L^4-Z^3)n$. Successive generations of the dendrimeric moiety can be produced by building up the dendrimer layers in succession, one after another according to the reaction conditions provided herein.

In some embodiments of formula (I) or (II), $L^1$ is absent. In some embodiments of formula (I) or (II), $L^1$ is a linker. In certain instances of formula (I) or (II), $L^1$ is a cleavable linker. In certain instances $L^1$ is a non-cleavable linker. As used herein, the term "cleavable linker" refers to a linker that can be selectively cleaved to produce two products. Application of suitable cleavage conditions to a molecule containing a cleavable linker that is cleaved by the cleavage conditions will produce two byproducts. A cleavable linker of the present disclosure is stable, e.g. to physiological conditions, until it is contacted with a cleavage-inducing stimulus, e.g., an agent such as an enzyme or other cleavage-inducing agent such as chemical agent, light, etc.

In some instances, the linker $L^1$ is a C1-C20 linker, such as an substituted or unsubstituted C1-C20 alkyl linker. In some embodiments of formula (I) or (II), $L^1$ is $-(CH_2)_{nx}-$, where nx is 1 to 20, such as 2 to 10, such as 2, 3, 4, 5, 6, 7, 8, 9 or 10. In some cases one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. In certain embodiments, the linker includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Linkers of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocycle groups, cleavable linker groups, combinations thereof, and substituted versions thereof.

In some embodiments, the linker includes a cleavable moiety (e.g., a chemically cleavable moiety, an enzymatically cleavable moiety (such as, but not limited to, a protease cleavable moiety, a glucuronidase cleavable moiety, a beta-lactamase cleavable moiety, etc.), a photocleavable moiety, and the like. In certain embodiments, the cleavable moiety is a para-amino-benzyloxycarbonyl group, a meta-aminobenzyloxycarbonyl group, a para-amino-benzyloxy group, a meta-amino-benzyloxy group, para-aminobenzyl, an acetal group, a disulfide, a hydrazine, a protease-cleavable moiety, a glucuronidase cleavable moiety, a beta-lactamase cleavable moiety, or an ester.

In certain embodiments of formula (I) or (II), the dendron branch point $J^1$ is a carbon atom, and n is 3. In certain instances, n is 3, and each pendant moiety $Z^2$ is a guanidine group, such that the compound of formula (I) or (II) terminates in three guanidine groups, where the guanidine groups are optionally protected as described above. In certain instances, n is 3, and $Z^2$ is a successive generation of $-J^1(L^2-Z^2)n$, such that the compound of formula (I) or (II) terminates in nine guanidine groups, where the guanidine groups are optionally protected as described above.

In certain other embodiments of formula (I) or (II), the dendron branch point $J^1$ is a nitrogen atom, and n is 2. In certain instances, n is 2, and each pendant moiety $Z^2$ is a guanidine group, such that the compound of formula (I) or (II) terminates in two guanidine groups, where the guanidine groups are optionally protected as described above. In certain instances, n is 2, and $Z^2$ is a successive generation of $-J(L^2-Z^2)n$, such that the compound of formula (I) or (II) terminates in four guanidine groups, where the guanidine groups are optionally protected as described above.

In certain embodiments of formula (I) or (II), $X^1$, and $X^2$ if present, are each independently selected from O, S, $NR^1$, $CR^2_2$, —C(O)O—, and —C(O)$NR^1$—. In some embodiments of formula (I), $X^1$ is O, S, $NR^1$, $CR^2_2$, —C(O)O—, and —C(O)$NR^1$—. In some embodiments of formula (I), $X^1$ is O. In some embodiments of formula (I), $X^1$ is S. In some embodiments of formula (I), $X^1$ is NH. In some embodiments of formula (I), $X^1$ is —C(O)O. In some embodiments of formula (I), $X^1$ is —C(O)NH. In some embodiments of formula (I), $X^1$ is derived from a C-nucleophile, e.g., $X^1$ is $CH_2$. In some embodiments of formula (II), $X^1$ is O, S, $NR^1$, $CR^2_2$, —C(O)O—, and —C(O)$NR^1$—. In some embodiments of formula (II), $X^1$ is O. In some embodiments of formula (II), $X^1$ is S. In some embodiments of formula (II), $X^1$ is NH. In some embodiments of formula (II), $X^1$ is —C(O)O. In some embodiments of formula (II), $X^1$ is —C(O)NH. In some embodiments of formula (II), $X^1$ is derived from a C-nucleophile, e.g., $X^1$ is $CH_2$. In some embodiments of formula (II), $X^2$ is O, S, $NR^1$, $CR^2_2$, —C(O)O—, and —C(O)$NR^1$—. In some embodiments of formula (II), $X^2$ is O. In some embodiments of formula (II), $X^2$ is S. In some embodiments of formula (II), $X^2$ is NH. In some embodiments of formula (II), $X^2$ is —C(O)O. In some embodiments of formula (II), $X^2$ is —C(O)NH. In some embodiments of formula (II), $X^2$ is derived from a C-nucleophile, e.g., $X^2$ is $CH_2$.

In some embodiments of formula (II), the compound is of formula (III):

(III)

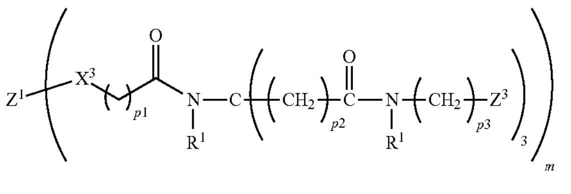

wherein:

$Z_1$ is a cargo moiety;

$X^3$ is a conjugation point;

$Z^3$ is a terminal group selected from a guanidine group, a protected guanidine group;

or $—(CH_2)_{p3}—Z^3$ is replaced with a successive generation of $—C((CH_2)_{p2}C(O)NR^1(CH_2)_{p3}—Z^3)_3$;

$R_1$ and $R_2$ are independently selected from H, an alkyl, and a substituted alkyl;

m is an integer from 1 to 20; and p1-p3 are each independently an integer from 1 to 10.

In certain embodiments of formula (III) $X^3$ is selected from O, S, $NR^1$, $CR^2_2$, —C(O)O—, and —C(O)$NR^1$—. In some embodiments of formula (III), $X^3$ is O. In some embodiments of formula (III), $X^3$ is S. In some embodiments of formula (III), $X^3$ is NH. In some embodiments of formula (III), $X^3$ is —O(O)O. In some embodiments of formula (III), $X^3$ is —C(O)NH. In some embodiments of formula (III), $X^3$ is derived from a C-nucleophile, e.g., $X^3$ is $CH_2$.

In some instances of formula (III), each pendant moiety $Z^3$ is a guanidine group. The guanidine groups of the subject compounds can be protected or masked (e.g., during synthesis) and then deprotected or unmasked according to any convenient strategy. In some embodiments of formula (III), $Z^3$ is an guanidine group (e.g., —NHC(=NH)—$NH_2$ or —NHC(=$NH_2$+)—$NH_2$). It is understood that the guanidine group can be charged or uncharged depending on the local environment, e.g., physiological aqueous conditions around or inside a cell. In some embodiments of formula (III), $Z^3$ is a protected guanidine group (e.g., —NHC(=$NX_a$)—$NHX_a$, where each $X_a$ is a guanidine protecting group, such as a Boc protecting group.

In some other embodiments of formula (III), $—(CH_2)_{p3}—Z^3$ is replaced with a successive generation of $—C((CH_2)_{p2}C(O)NR^1(CH_2)_{p3}—Z^3)_3$. Accordingly, a successive generation includes a second branch point (Carbon atom), a second linking moiety, and terminates in a pendant moiety $Z^3$ as described above. Or alternatively, $—(CH_2)_{p3}—Z^3$ is replaced with another a successive generation of $—C((CH_2)_{p2}C(O)NR^1(CH_2)_{p3}—Z^3)_3$. Successive generations of the dendrimeric moiety can be produced by building up the dendrimer layers in succession, one after another according to the reaction conditions provided herein.

In some embodiments of formula (III), each of p1-p3 is 1 or more, such as 2 or more, 3 or more, 4 or more, 5 or more, 6 or more, 7 or more, 8 or more, or 9 or more In some embodiments of formula (III), each of p1-p3 is 10 or less, such as 9 or less, 8 or less, 7 or less, 6 or less, 5 or less, 4 or less, 3 or less, or even less. In some embodiments of formula (III), p1 is 2 to 10, such as 2 to 8, 2 to 7, 2 to 6, 2 to 5, or 2 to 4. In some cases, p1 is 1, 2, 3, 4, 5, 6, 7, 8, 9 or 10. In some cases, p1 is 5. In some embodiments of formula (III), p2 is 2 to 10, such as 2 to 8, 2 to 7, 2 to 6, 2 to 5, or 2 to 4. In some cases, p2 is 1, 2, 3, 4, 5, 6, 7, 8, 9 or 10. In some cases, p2 is 2. In some embodiments of formula (III), p3 is 2 to 10, such as 2 to 8, 2 to 7, 2 to 6, 2 to 5, or 2 to 4. In some cases, p3 is 1, 2, 3, 4, 5, 6, 7, 8, 9 or 10. In some cases, p3 is 2. In some cases, p3 is 6.

In some embodiments of formula (III), $R_1$ and $R_2$ are independently selected from H, and alkyl. In some cases, $R_1$ and $R_2$ are both H. In some cases, $R_1$ and $R_2$ are both alkyl. In some cases $R_1$ is H, and $R_2$ is alkyl. In some cases, $R_1$ alkyl, and $R_2$ is H.

In some embodiments of formula (III), the compound is of the formula (IV):

(IV)

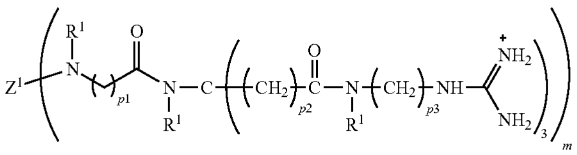

wherein:

$Z_1$ is a cargo moiety;

each $R^1$ is independently selected from H, an alkyl, and a substituted alkyl;

m is an integer from 1 to 20; and p1-p3 are each independently an integer from 1 to 10.

In certain embodiments of formula (IV), each $R^1$ is H. In certain embodiments each $R^1$ is H, m is 1, p1 is an integer from 2 to 10, p2 is 2, and p3 is an integer form 2 to 10. In certain cases, each $R^1$ is H, m is 1, p1 is 5, p2 is 2 and p3 is an integer from 2 to 6.

In some embodiments of any one of formulae (I)-(IV), m is 2 or more, such as 3 or more, 4 or more, 5 or more, 6 or more, 7 or more, 8 or more, 9 or more, or 10 or more. In some embodiments of any one of formulae (I)-(IV), m is 10 or less, such as 9 or less, 8 or less, 7 or less, 6 or less, 5 or less, 4 or less, 3 or less, or even less. In some embodiments of any one of formulae (I)-(IV), m is 1 to 10, such as 1 to 8, 1 to 6, 1 to 4, or 1 to 2. In some embodiments of any one of formulae (I)-(IV), m is 1 to 5. In certain cases, of any one of formulae (I)-(IV), m is 1. In certain cases, of any one of formulae (I)-(IV), m is 2. In certain cases, of any one of formulae (I)-(IV), m is 3. In certain cases, of any one of formulae (I)-(IV), m is 4. In certain cases, of any one of formulae (I)-(IV), m is 5.

In some embodiments of any one of formulae (I)-(IV), $Z^1$ is a cargo moiety (e.g., as described herein. Any convenient cargo moiety can find use in the instant application, as described herein. In certain cases, the cargo moiety is selected from a therapeutic agent, an affinity ligand, a diagnostic agent, a detectable label, a chelating agent, a peptidyl tag, and a clearance modifying agent. In certain cases, the cargo agent is a therapeutic agent. In other cases, the cargo moiety is an affinity ligand. In certain cases, the cargo moiety is a diagnostic agent. In certain cases, the cargo moiety is a detectable label. In certain cases, the cargo moiety is a chelating agent. In certain cases, the cargo moiety is a peptidyl tag. In certain other cases, the cargo moiety is a clearance modifying agent.

In certain embodiments of any one of formulae (I)-(IV), the cargo moiety is selected from an antibiotic, an antiviral drug, a chemotherapeutic drug, a dye, a peptide, and a nucleoside.

In certain embodiments of any one of formulae (I)-(IV), the cargo moiety is an antibiotic. In certain cases, any one of formulae (I)-(IV) includes an antibiotic agent as described herein above. In certain cases, the antibiotic is selected from vancomycin, linezolid, azithromycin, daptomycin, colistin, eperezolid, fusidic acid, rifampicin, tetracyclin, fidaxomicin, clindamycin, lincomycin, rifalazil, and clarithromycin. In certain cases, the antibiotic is vancomycin.

In certain embodiments of any one of formulae (I)-(IV), the cargo moiety is a chemotherapeutic drug. In certain cases, any one of formulae (I)-(IV) includes a chemotherapeutic drug agent as described herein above.

In certain embodiments the subject compound is selected from one of the following structures:

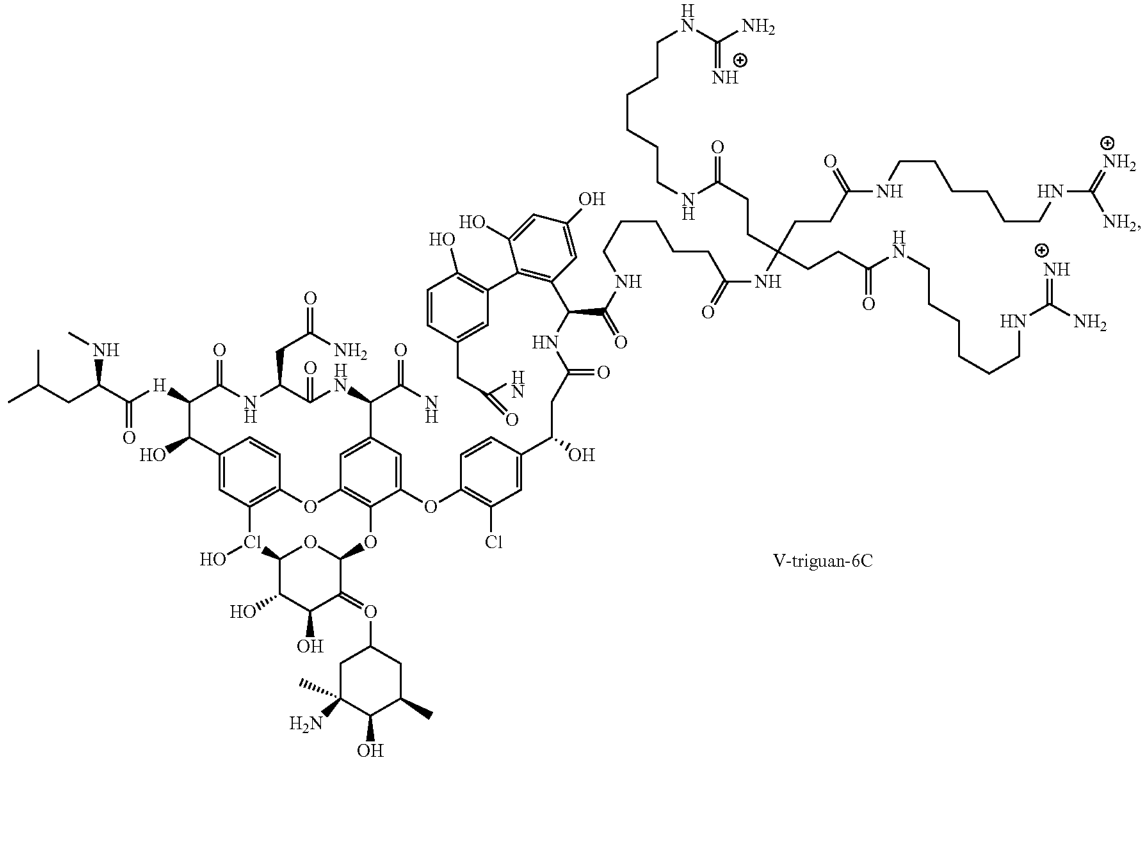

and

V-triguan-6C

-continued

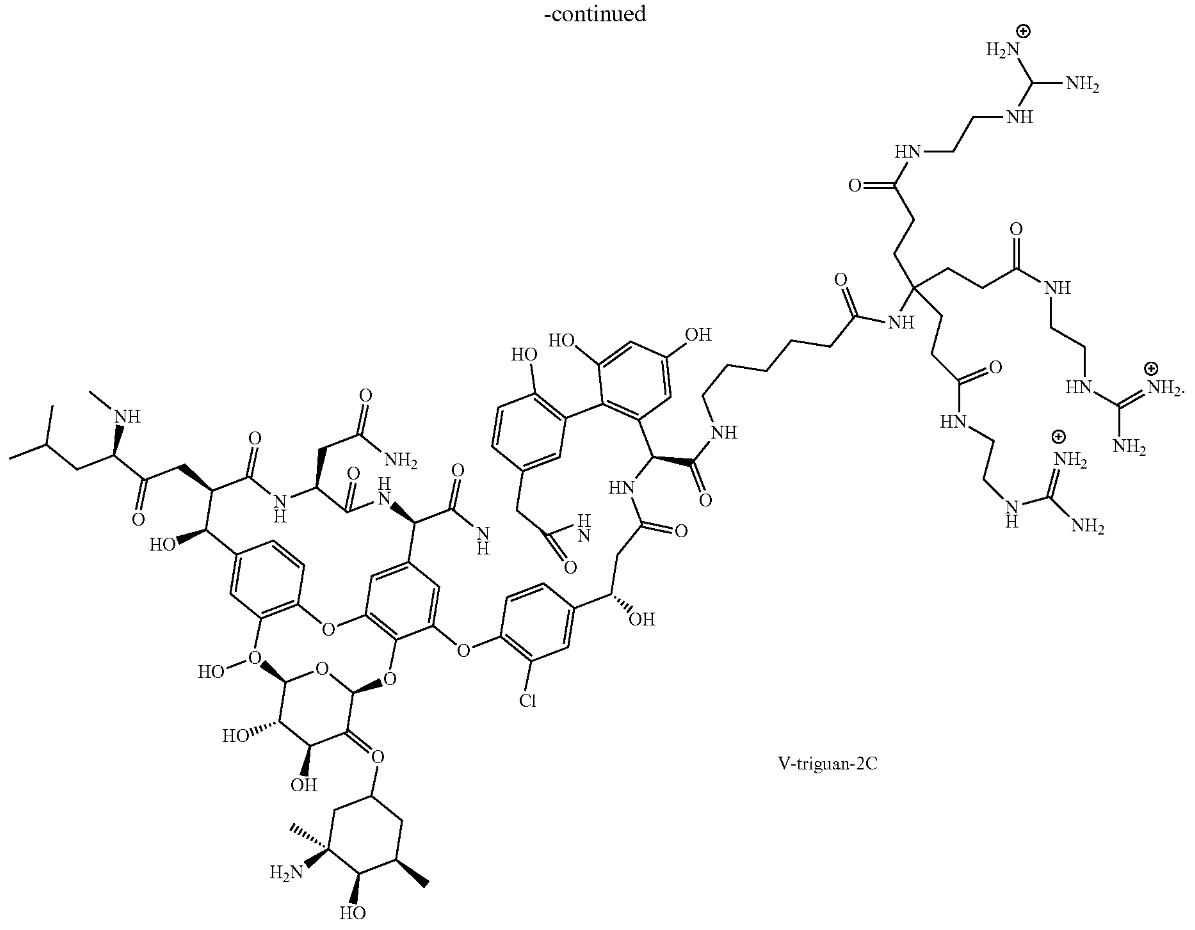

V-triguan-2C

Aspects of the disclosure also include reversibly conjugated dendrimeric moieties and branched structures, wherein compounds include pendant cargo molecules. In certain embodiments, the reversibly conjugated dendrimeric or branched moiety includes one or more terminal cargo moieties, wherein the cargo moiety may be bonded to a dendrimer core via a linker (e.g., as described herein). In certain cases the dendrimer core includes one or more successive generations of linkages terminating in one or more cargo moieties.

Accordingly, in one embodiment, there is provided a compound of the formula (Va) or (Vb):

$$J^2 \leftarrow L^2\text{-}Z^2—Z^1)_{n1} \quad \text{(Va)}$$

$$J^2 \leftarrow L^2\text{-}J^3 \leftarrow L^2\text{-}Z^2—Z^1)_{n1})_{n2} \quad \text{(Vb)}$$

wherein:

$J^2$ is a dendrimer core;

$J^3$ is a branching point;

each $L^2$ is a linker;

$Z^2$ is a linker moiety or an atom substituted by a pendant group selected from a guanidine group, a protected guanidine group $Z^1$ is -($L^2$-$Z^2$—$Z^1$) or -$J^3$($L^2$-$Z^2$—$Z^1$) or a cargo moiety;

n1 is an integer from 2 to 4; and n2 is an integer from 2 to 4.

In some instances of formula (Va) or (Vb), each linker $L^2$ is a C1-C20 linker, such as an substituted or unsubstituted C1-C20 alkyl linker or a C2-C20 linker comprising one or more double or triple bonds. In some cases, $L^2$ is a non-cleavable linker, e.g., a non-cleavable linker as described herein. In some embodiments of formula (I), $L^2$ is —$(CH_2)_{nx}$—, where nx is 1 to 20, such as 2 to 10, such as 2, 3, 4, 5, 6, 7, 8, 9 or 10. In some cases one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone.

In some instances of formula (Va) or (Vb), $Z^2$ is a group or an atom associated with a pendant guanidine group. The guanidine groups of the subject compounds can be protected or masked (e.g., during synthesis) and then deprotected or unmasked according to any convenient strategy. In some embodiments of formula (Va) or (Vb), in $Z^2$ the pendant group is a guanidine group (e.g., a linking guanidine group). It is understood that the guanidine group can be charged or uncharged depending on the local environment, e.g., physiological aqueous conditions around or inside a cell.

In some embodiments of formula (Va or (Vb), the compound is of the formula (VIa) or (VIb):

$$J^2 \leftarrow L^3\text{-}X^2\text{-}L^4\text{-}Z^2—Z^1)_{n1} \quad \text{(VIa)}$$

$$J^2 \leftarrow L^3\text{-}X^2\text{-}J^3 \leftarrow L^3\text{-}X^2\text{-}L^4\text{-}Z^2—Z^1)_{n1})_{n2} \quad \text{(VIb)}$$

wherein:

$J^2$ is a dendrimer core;

$J^3$ is a branching point;

each $L^3$ is a linker;

each $X^2$ is a conjugation point;

each $L^4$ is a linker comprising 2-10 atoms, wherein the linker optionally comprises one or more additional branching points;

$Z^2$ is a group or an atom substituted to a pendant group selected from a guanidine group, a protected guanidine group, an amino group, and an oligophosphotriester;

$Z^1$ is -(L2-Z2-Z1) or -J3(L2-Z2-Z1) or a cargo moiety;

n1 is an integer from 2 to 4; and n2 is an integer from 2 to 4.

In some instances of formula (VIa) or (VIb), the linker $L^3$ is a C1-C20 linker, such as an substituted or unsubstituted C1-C20 alkyl linker or a C2-C20 linker comprising one or more double or triple bonds. In some cases, $L^2$ is a non-cleavable linker, e.g., a non-cleavable linker as described herein. In some embodiments of formula (I), $L^2$ is $—(CH_2)_{nx}—$, where nx is 1 to 20, such as 2 to 10, such as 2, 3, 4, 5, 6, 7, 8, 9 or 10. In some cases one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. In some embodiments, the carbon chain is interrupted by one or more atoms selected from sulfur, nitrogen or oxygen.

In certain embodiments of formula (VIa) or (VIb), $L^4$ is a C1-C20 linker, such as an substituted or unsubstituted C1-C20 alkyl linker or a C2-C20 linker comprising one or more double or triple bonds. In some cases, $L^4$ is a non-cleavable linker, e.g., a non-cleavable linker as described herein. In some embodiments of formula (VIa) or (VIb), $L^4$ is $—(CH_2)_{nx}—$, where nx is 1 to 20, such as 2 to 10, such as 2, 3, 4, 5, 6, 7, 8, 9 or 10. In some cases one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. In certain embodiments of formula (VIa) or (VIb), $L^4$ is selected from $—(CH_2)_{nx}—$, and $—OC(O)CH(NR^3)(CH_2)_{nx})—$, wherein each $R^3$ is independently selected from H, alkyl, substituted alkyl, or a branching point, and nx is 1 to 20, such as 2 to 10, such as 2, 3, 4, 5, 6, 7, 8, 9 or 10. In some cases, $L^4$ is $—OC(O)CH(NR^3)(CH_2)_{nx})—$, where $R^3$ is H and nx is an integer from 2 to 10. In some cases, nx is less than 10, such as 9, 8, 7, 6, 5, 4, 3 or 2. In certain cases, nx is from 2 to 6. In certain cases, nx is 6. In certain cases, nx is 5. In certain cases, nx is 4. In certain cases, nx is 3. In certain cases, nx is 3. In certain cases, nx is 2.

In certain embodiments of formula (VIa) or (VIb), $L^4$ and $Z^2$ together comprise an amino acid residue selected from lysine and arginine, wherein the C-terminus is conjugated to $X^2$. In certain cases, the amino residue is lysine. In certain cases, the amino residue is D-lysine. In certain cases, the amino residue is L-lysine. In certain cases, the amino acid is arginine. In certain cases, the amino acid is D-arginine. In certain cases, the amino acid is L-arginine. In certain cases, $L^4$ and $Z^2$ together form a branched derivative of lysine or arginine. In some cases, the branched derivative of lysine or arginine is branched through the amine group alpha to the C-terminus. In certain cases, the branched arginine or lysine derivative comprises one or more additional amino acids. In certain cases, the branched arginine or lysine derivative comprises one or more guanidine groups.

In some instances of formula (VIa) or (VIb), in $Z^2$ the pendant groups is a guanidine group. The guanidine groups of the subject compounds can be protected or masked (e.g., during synthesis) and then deprotected or unmasked according to any convenient strategy. In some embodiments of formula (VIa) or (VIb), in $Z^2$ the pendant group is a guanidine group (e.g., a linking guanidine group). It is understood that the guanidine group can be charged or uncharged depending on the local environment, e.g., physiological aqueous conditions around or inside a cell.

In certain embodiments of any one of formulae (Va)-(VIb), the dendrimer core $J^2$ is a carbon atom. In certain cases of formula (Va) and (VIa), the dendrimer core $J^2$ is a carbon atom, and n1 is 3, such that the compound of formula (Va) or (VIa) terminates in three cargo moieties. In certain cases of formula (Va) and (VIa), the dendrimer core $J^2$ is a carbon atom, and n1 is 4, such that the compound of formula (Va) or (VIa) terminates in four cargo moieties.

In certain cases of formula (Vb) and (VIb), the dendrimer core $J^2$ and branching point $J^3$ are both carbon atoms. In certain cases of formula (Vb) and (VIb), $J^2$ and $J^3$ are both carbon atoms, and n1 and n2 are each 3, such that the compound of formula (Vb) or (VIb) terminates in nine cargo moieties. In certain cases of formula (Vb) and (VIb), $J^2$ and $J^3$ are both carbon atoms, and n1 and n2 are each 4, such that the compound of formula (Vb) or (VIb) terminates in sixteen cargo moieties.

In certain embodiments of any one of formulae (Va)-(VIb), the dendrimer core $J^2$ is a nitrogen atom. In certain cases of formula (Va) and (VIa), the dendrimer core $J^2$ is a nitrogen atom, and n1 is 2, such that the compound of formula (Va) or (VIa) terminates in two cargo moieties. In certain cases of formula (Va) and (VIa), the dendrimer core $J^2$ is a nitrogen atom, and n1 is 3, such that the compound of formula (Va) or (VIa) terminates in three cargo moieties.

In certain cases of formula (Vb) and (VIb), the dendrimer core $J^2$ and branching point $J^3$ are both nitrogen atoms. In certain cases of formula (Vb) and (VIb), $J^2$ and $J^3$ are both nitrogen atoms, and n1 and n2 are each 2, such that the compound of formula (Vb) or (VIb) terminates in four cargo moieties. In certain cases of formula (Vb) and (VIb), $J^2$ and $J^3$ are both nitrogen atoms, and n1 and n2 are each 3, such that the compound of formula (Va) or (VIb) terminates in nine cargo moieties.

In certain embodiments of any one of formulae (Va)-(VIb), $X^2$ is selected from O, S, $NR^1$, $CR^2_2$, —C(O)O—, and $—C(O)NR^1—$. In some embodiments of any one of formulae (Va)-(VIb), $X^2$ is O. In some embodiments of any one of formulae (Va)-(VIb), $X^2$ is S. In some embodiments of any one of formulae (Va)-(VIb), $X^2$ is NH. In some embodiments of any one of formulae (Va)-(VIb), $X^2$ is —C(O)O. In some embodiments of any one of formulae (Va)-(VIb), $X^2$ is —C(O)NH. In some embodiments of any one of formulae (VIa)-(VIb), $X^2$ is derived from a C-nucleophile, e.g., $X^2$ is $CH_2$.

In certain embodiments of formula (VIa) or (VIb), the compound is of formula (VIIa) or (VIIb):

(VIIa)

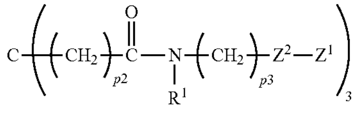

(VIIb)

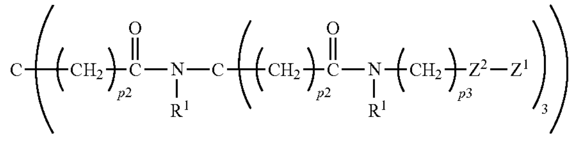

wherein:

$Z^1$ is a cargo moiety;

$Z^2$ is a group or an atom substituted to a pendant group selected from a guanidine group or a protected guanidine group, $R^1$ is selected from H, an alkyl, and a substituted alkyl; and p2-p3 are each independently an integer from 1 to 10.

In certain embodiments of formula (VIIa) or (VIIb), each $R^1$ is H. In certain embodiments each $R^1$ is H, m is 1, p2 is an integer from 2 to 10, and p3 is an integer form 2 to 10. In certain cases, each $R^1$ is H, p2 is 2 and p3 is an integer from 2 to 6.

In some instances of formula (VIIa) or (VIIb), $Z^2$ is a guanidine group. The guanidine groups of the subject compounds can be protected or masked (e.g., during synthesis) and then deprotected or unmasked according to any convenient strategy. In some embodiments of formula (VIIa) or (VIIb), $Z^2$ is a guanidine group (e.g., a linking guanidine group). It is understood that the guanidine group can be charged or uncharged depending on the local environment, e.g., physiological aqueous conditions around or inside a cell.

In some embodiments of any one of formulae (Va)-(VIIb), $Z^1$ is a cargo moiety (e.g., as described herein. Any convenient cargo moiety can find use in the instant application. Cargo moieties of interest include without limitation small molecule drugs including without limitation antibiotics, antiviral, chemotherapeutic agents, peptides, nucleosides, polynucleotides, proteins, siRNA, mRNA, plasmids, metals, imaging agents, sensors and the like. In certain cases, the cargo moiety is selected from a therapeutic agent, an affinity ligand, a diagnostic agent, a detectable label, a chelating agent, a peptidyl tag, and a clearance modifying agent. In certain cases, the cargo agent is a therapeutic agent. In other cases, the cargo moiety is an affinity ligand. In certain cases, the cargo moiety is a diagnostic agent. In certain cases, the cargo moiety is a detectable label. In certain cases, the cargo moiety is a chelating agent. In certain cases, the cargo moiety is a peptidyl tag. In certain other cases, the cargo moiety is a clearance modifying agent.

In certain embodiments of any one of formulae (Va)-(VIIb), the cargo moiety is selected from an antibiotic, an antiviral drug, a chemotherapeutic drug, a dye, a peptide, and a nucleoside.

In certain embodiments of any one of formulae (Va)-(VIIb), the cargo moiety is an antibiotic. In certain cases, any one of formulae (Va)-(VIIb) includes an antibiotic agent as described herein above. In certain cases, the antibiotic is selected from vancomycin, linezolid, azithromycin, daptomycin, colistin, eperezolid, fusidic acid, rifampicin, tetracyclin, fidaxomicin, clindamycin, lincomycin, rifalazil, and clarithromycin. In certain cases, the antibiotic is vancomycin.

In certain embodiments of any one of formulae (Va)-(VIIb), the cargo moiety is a chemotherapeutic drug. In certain cases, any one of formulae (Va)-(VIIb) includes a chemotherapeutic drug agent as described herein above.

Pharmaceutical Compositions

The herein-discussed conjugates can be formulated using any convenient excipients, reagents and methods. Compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed, Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the subject conjugates are formulated in an aqueous buffer.

Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In some cases, the formulation is stored at about 4° C. In some cases, the formulation is stored at −20° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In some embodiments, the conjugate is administered to individuals in a formulation with a pharmaceutically acceptable excipient(s). The subject molecules, as well as additional therapeutic agents as described herein for combination therapies, can be administered orally, topically, subcutaneously, intramuscularly, parenterally, by inhalation, IV, IP or other routes. The subject complexes and additional therapeutic agents may be administered by the same route of administration or by different routes of administration. The therapeutic agents can be administered by any suitable means including, but not limited to, for example, oral, rectal, nasal, topical (including transdermal, aerosol, buccal and sublingual), ocular, vaginal, parenteral (including subcutaneous, intramuscular, intravenous and intradermal), intravesical or injection into an affected organ.

The subject conjugates may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

A therapeutically effective amount of a compound in this context can be regarded as an amount that is effective in reducing the incidence (e.g., the likelihood that an individual will develop) of a disorder by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or to a placebo-treated individual.

Methods of Preparation

Any convenient methods can be utilized in preparation of the subject conjugate compounds. In some cases, the subject conjugate can be synthesized by coupling a cargo moiety of interest with a reactive functional group on a subject dendron derivative (see, e.g., Scheme 1 as disclosed herein). In some cases, the conjugation point on the cargo moiety is a carboxylic acid, and the reactive functional group on the subject dendron derivative is an amino group. In certain cases, the conjugation point on the cargo moiety may be without limitation selected from a hydroxyl group, an amino group, an alkyne, an azide, an ester, an aldehyde, and a thiol. Additional reactive functional groups of interest which may be incorporated for use in the subject methods, include, but are not limited to, a thiol, an alkyne, a cyclooctyne, an azide, a phosphine, a maleimide, an alkoxyamine, an aldehyde and protected versions thereof, and precursors thereof. In certain embodiments, the reactive functional group on the dendron derivative is a thiol. In certain embodiments, the reactive functional group is a protected thiol, such as a dithiopyridyl protected thiol.

In certain embodiments the dendron derivative includes a protected thiol. In certain embodiments of the method, the method further comprises deprotecting the dendron derivative to produce a reactive functional group and conjugating the reactive functional group to a cargo moiety. Any convenient conjugation chemistries and chemoselective functional group pairs can be utilized to conjugate a subject dendron derivative to a cargo moiety of interest.

In certain cases, preparation of the subject dendron derivative is adapted from previous work by Wender and coworkers (Wender, P. A., Kreider, E., Pelkey, E. T., Rothbard, J., and VanDeusen, C. L. (2005) Dendrimeric Molecular Transporters: Synthesis and Evaluation of Tunable Polyguanidino Dendrimers that Facilitate Cellular Uptake. Organic letters, 7(22), 4815-4818.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, N.Y. 1999, in "The Peptides"; Volume 3 (editors: E. Gross and J. Meienhofer), Academic Press, London and New York 1981, in "Methoden der organischen Chemie", Houben-Weyl, 4th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Exemplary synthetic methods for the subject compounds are described herein. These methods can be adapted to synthesize compounds described herein.

Methods of Use

Also provided are methods of using the subject conjugate compounds. In some cases, the compound may find use as therapeutic agents. In certain cases, the subject conjugate compounds find use as antimicrobial agents effective against one or both of antibiotic-resistant Gram-positive bacteria, and against Gram-negative bacteria.

In certain embodiments, there is provided a method of delivering a cargo moiety to a cell, the method comprising contacting a cell with a subject compound (e.g., a guanidinium-rich dendrimeric or branched conjugate as described herein), under conditions to deliver the cargo moiety to the cell.

In certain embodiments of the method, the cell is a bacterial cell population, and the contacting reduces the bacterial cell population. In certain cases, the bacterial cell population comprises one or more of, persister cells, antibiotic-resistant bacteria, biofilms, intracellular bacteria, MRSA, MRSE, VRE, or *Enterococcus.*

In certain embodiments of the method, the bacterial cell population comprises Gram-negative bacteria resistant to an antibiotic, and the compound comprises the antibiotic, or a derivative thereof, in an effective dose non-toxic to human cells.

In certain embodiments of the method, the bacterial cell population comprises Gram-positive bacteria resistant to an antibiotic, and the compound comprises the antibiotic, or a derivative thereof, in an effective dose non-toxic to human cells.

In yet other embodiments of the method, the bacterial cell population comprises Gram-positive bacteria, and Gram-negative bacteria, and the contacting reduces the Gram positive bacteria, and the Gram-negative bacteria.

In certain cases, the bacteria is resistant to an antibiotic (e.g., as described herein), and the compound comprises the antibiotic, or a derivative thereof, in an effective dose non-toxic to human cells.

In certain cases, the bacteria is resistant to vancomycin, and the compound comprises vancomycin, or a derivative thereof, in an effective dose non-toxic to human cells.

In some embodiments, there is provided a method of treating a subject for a disease condition, the method comprising administering to the subject an effective amount of the subject compound (e.g., as described herein) to treat the subject for the disease condition.

In some cases, the disease or condition is an infectious disease. In some cases, the disease or condition is a bacterial infection. In some cases, the disease or condition is a viral infection. In some cases, the disease or condition is cancer.

Methods are provided for the use of guanidinium-rich dendrimeric antibiotic conjugates as antimicrobial agents, including without limitation conjugates of vancomycin and vancomycin derivatives and analogs. In some embodiments the conjugate is as shown in Scheme 1 (e.g., V-triguan-2C, or V-triguan-6C). Such conjugates can be administered alone or in combination with other active agents to a patient suffering from or predisposed to infections that are resistant or tolerant to conventional antibiotics, including infections resistant to vancomycin, methicillin, etc. The infection is treated by contacting the infectious bacterial cell population with a dose and for a period of time sufficient to reduce the population of microbial pathogens, in vivo or in vitro, including for example medical surfaces.

An effective dose may be the dose that achieves substantial depletion or eradication of the bacterial cell population, which result in the killing of substantially all of the bacterial cells, e.g. at least about 99%, at least about 99.9%, at least about 99.99%, or more. The effective dose may be based on the MIC, or MBEC, although is typically a higher dose to ensure eradication. The effective dose of a conjugated antibiotic is generally at least about 5-fold less than the effective dose for the corresponding non-conjugated antibiotic, and may be 10-fold less, 50-fold less, 100-fold less, or less. The effective time for eradication is also decreased, for example decreased at least 2-fold, at least about 3-fold, at least about 4-fold, at least about 5-fold, or more.

An effective dose of a conjugated antibiotic may be a dose that achieves a concentration at the target site of at least about 0.01 mM, at least about 0.1 mM, at least about 1 mM, at least about 5 mM, at least about 10 mM, at least about 50 mM, at least about 100 mM, at least about 500 mM, at least about 1 mM, at least about 5 mM, at least about 10 mM.

In some embodiments, the effective daily dose can range from about 0.5 mg to about 500 g, for example at least about 0.5 mg, at least about 1 mg, at least about 5 mg, at least about 10 mg, at least about 50 mg, at least about 100 mg, at least about 500 mg, at least about 1 g, at least about 5 g, at least about 10 g, at least about 50 g, at least about 100 g, and not more than about 500 g.

In some embodiments an infection for treatment comprises a bacterial cell population in which at least about 5% of the bacteria are resistant or tolerant to antibiotics, at least about 10%, at least about 20%, at least about 30%, at least about 50%, at least about 75%, at least about 85%, at least about 95% resistant or tolerant bacteria, where resistant or tolerant bacteria may include, for example: persister cells; MRSA; MRSE; GRE; ORSA; Gram-negative bacteria when the antibiotic is vancomycin or a derivative thereof; biofilms; vancomycin resistant bacteria; etc.

In some embodiments the infection is present on the skin, i.e. a wound. In such embodiments, a topical formulation is optionally utilized for treatment. An advantage of the conjugated antibiotic provided herein is the enhanced bioavailability for topical formulations that is provided.

In some embodiments the antibiotic resistant or tolerant bacteria are present as a biofilm. In some embodiments the biofilm is substantially comprised of Gram-positive bacteria. In some embodiments the biofilm is substantially comprised of Gram-negative bacteria. In some embodiments a biofilm is present on implantable medical devices, which are particularly susceptible to biofilm formation.

In some embodiments, the effective daily dose is provided in a unit dosage formulation in any increment. As non-limiting illustrative examples: administration of one 1.6 mg capsule, two 800 pg capsules, etc. can be performed twice in one day to deliver a daily dose of 3.2 mg; or thrice in one day to deliver a daily dose of 4.8 mg. As another non-limiting example, the use of 1 mg capsules facilitates any dose (e.g., a daily dose) with a multiple of (1 mg) (e.g., 2 mg, 3 mg, 4 mg, etc.)

A treatment regime can entail administration daily (e.g., once, twice, thrice, etc. daily), every other day (e.g., once, twice, thrice, etc. every other day), semi-weekly, weekly, once every two weeks, once a month, etc. In another example, treatment can be given as a continuous infusion. Unit doses are usually administered on multiple occasions. Intervals can also be irregular as indicated by monitoring clinical symptoms. Alternatively, the unit dose can be administered as a sustained release formulation, in which case less frequent administration is required. Dosage and frequency may vary depending on the patient. It will be understood by one of skill in the art that such guidelines will be adjusted for localized administration, e.g. intranasal, inhalation, rectal, etc., or for systemic administration, e.g. oral, rectal (e.g., via enema), i.m. (intramuscular), i.p. (intraperitoneal), i.v. (intravenous), s.c. (subcutaneous), transurethrally, and the like.

The conjugated antibiotic can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of the subject antibiotic conjugate includes use in combination with another therapeutic agent, e.g., a bactericidal or bacteriostatic agent. Therapeutic formulations can be prepared for storage by mixing the subject antibiotic conjugate with optional physiologically acceptable carriers, excipients or stabilizers (Remington's Pharmaceutical Sciences 16th edition, Osol, A. Ed. (1980)), in the form of lyophilized formulations or aqueous solutions. The subject antibiotic conjugate composition will be formulated, dosed, and administered in a fashion consistent with good medical practice. The "effective amount" to be administered will be governed by considerations such as those cited above (e.g, severity of disease etc.), and is the minimum amount necessary to prevent and/or reduce the targeted biofilm.

Formulations of the subject dendrimeric antibiotic conjugates are administered to a host suffering from or predisposed to a microbial infection. Administration may be topical, localized or systemic, depending on the specific microorganism, preferably it will be localized. Generally the dose of biofilm inhibitor will be sufficient to decrease the microbial population in the biofilm by at least about 50%, usually by at least 1 log, and may be by 2 or more logs of release. The compounds of the present invention are administered at a dosage that reduces the microbial population while minimizing any side-effects. It is contemplated that the composition will be obtained and used under the guidance of a physician for in vivo use.

The subject antibiotic conjugates are also useful for in vitro formulations to dissolve microbial biofilms. For example, biofilm inhibitors may be added to hospital equipment, e.g. ventilation, water processing, etc.

The susceptibility of a particular microbe to the subject antibiotic conjugates may be determined by in vitro testing. Typically a culture of the microbe is combined with agents at varying concentrations for a period of time sufficient to allow the subject antibiotic conjugates to act, usually between about one hour and one day. The attached microbes are then counted, and the level of viability determined.

Various methods for administration may be employed. The formulation may be given orally, or may be injected intravascularly, subcutaneously, peritoneally, by aerosol, ophthalmically, intra-bladder, topically, etc. For example, methods of administration by inhalation are well-known in the art. The dosage of the therapeutic formulation will vary widely, depending on the specific biofilm inhibitor to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi weekly, etc. to maintain an effective dosage level. In many cases, oral administration will require a higher dose than if administered intravenously.

In certain embodiments the subject methods involve delivery of a cargo moiety (e.g., as described herein) to a cell (e.g., in vitro or in vivo). In some embodiments, the method includes, contacting a cell with a subject conjugate compound (e.g., as described herein), under conditions in which the cargo moiety is cleaved from the dendrimeric or branched moiety and diffuses from the dendrimeric compound. In some instances, the dendrimeric or branched moiety includes a plurality of therapeutic agents. In certain other instances, the cargo moiety includes a plurality of dendrimeric or branched moieties.

Any convenient cargo moiety (e.g., therapeutic agents) may be delivered according to the subject methods. Therapeutic agents of interest include, but are not limited to, those convenient cargo moieties described herein. In certain instances, the therapeutic agent is a pharmaceutical agent, am imaging agent, a plasmid, a polynucleotide, a polypeptide, a chemotherapeutic agent, a pro-drug, or combination thereof. The cargo moieties may be attached to the dendrimeric or branched moiety compound via a cleavable or non-cleavable linker. In certain instances, the cargo moiety remains linked to the dendrimeric or branched moiety compound after delivery to the cell. In some embodiments, the cargo moieties (e.g., therapeutic agents) are cleaved under intracellular reducing conditions. In certain embodiments, the cargo moieties (e.g., therapeutic agents) are enzymatically cleaved. In some embodiments, the cargo moieties (e.g., therapeutic agents) are cleaved under intracellular pH conditions. In some embodiments, the cargo moieties (e.g., therapeutic agents) are cleaved under intracellular degradation conditions. In some embodiments, release of desired therapeutic cargo results in its activation for biological activity, e.g. pro-drug delivery. A variety of intracellular conditions of target cells may be adapted for use in the subject methods and compositions.

Any convenient configurations of dendrimeric or branched moieties, types of linkers and modifications, and cargo moieties may be selected to provide for a desired drug release mechanisms and drug delivery, e.g., over an extended period of time. In additional embodiments, the delivered cargo can consist of an inactive pro-drug entity (ies) which becomes biologically activated upon release from the dendrimeric or branched compound. In further embodiments, release and activation of pro-drug cargo from the subject compounds may be dependent upon delivery to appropriate target cells, tissues, organs, etc. which contain the necessary activating agent as a means to limit pro-drug activation to desired cellular locations.

Any convenient cells can be targeted for delivery of a cargo moiety according to the subject methods. The cell may be in a biological sample. The term "sample" as used herein relates to a material or mixture of materials, typically, although not necessarily, in liquid form, containing one or more analytes of interest. In one embodiment, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. In some cases, the sample is derived from a human. The term "sample" may also refer to a "biological sample". As used herein, the term "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In certain embodiments, the sample has been removed from an animal or plant. Biological samples of the invention include cells. The term "cells" is used in its conventional sense to refer to the basic structural unit of living organisms, both eukaryotic and prokaryotic, having at least genetic material and a cell membrane. In certain embodiments, cells include prokaryotic cells, such as from bacteria. In other embodiments, cells include eukaryotic cells, such as cells obtained from biological samples from animals, plants or fungi.

Aspects of the present disclosure include a method of delivering a cargo moiety to a cell. In some instances, the method comprises contacting a cell with a guanidinium-rich dendrimeric or branched compound (e.g., as described herein) that includes the cargo moiety. The method can be performed in vitro or in vivo. The guanidinium-rich dendrimeric or branched compounds can provide for passage of the conjugate (e.g., including the attached cargo moiety) through the cell membrane and into the cell. As such, in some cases, the method is an intracellular delivery method. In certain instances, the cargo moiety is linked to the guanidinium-rich dendrimeric or branched compounds via a cleavable linker (e.g., $L^1$) and the method further comprises cleaving the linker (e.g., $L^1$) to release the cargo moiety.

In some embodiments, the cell is in vivo and the cargo moieties (e.g., therapeutic agents) are released and/or diffuse from the dendrimeric or branched moieties to achieve immediate, delayed, or constant therapeutic level in the cell over a suitable period of time, e.g., an extended period of time suitable for achieving a therapeutic result. Also provided are methods of treating a subject for a disease condition, the method comprising administering to the subject an effective amount of a pharmaceutical composition (e.g., as described herein) to treat a subject for the disease condition.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is number average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present disclosure. All such modifications are intended to be within the scope of the claims appended hereto.

Example 1

Dendrimeric Conjugate Synthesis

Compounds may be synthesized using any convenient method. Methods which can be adapted for use in preparing compounds of this disclosure includes the exemplary synthetic methods described in Examples 1, and those methods described by Wender, P. A., Kreider, E., Pelkey, E. T., Rothbard, J., and VanDeusen, C. L. (2005) Dendrimeric Molecular Transporters: Synthesis and Evaluation of Tunable Polyguanidino Dendrimers that Facilitate Cellular Uptake. Organic letters, 7(22), 4815-4818. Many general references providing commonly known chemical synthetic schemes and conditions useful for synthesizing the disclosed compounds are also available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978). Reactions may be monitored by thin layer chromatography (TLC), LC/MS and reaction products characterized by LC/MS and $^1$H NMR. Intermediates and final products may be purified by silica gel chromatography or by HPLC.

Scheme 1 shows the synthesis of an exemplary dendrimeric conjugate of vancomycin, which can be adapted for use in preparing compounds of this disclosure. As seen in Scheme 1, tri-acid Abt1 was treated with a tert-butyloxycarbonyl (N-Boc) diamine to afford the N-boc protected nitro derivative Abt2. The nitro derivative Abt2 was then subject to Raney nickel reduction conditions to obtain the free amine Abt3. The free amine of Abt3 was then coupled to Cbz-Ahx-OH to afford the carboxybenzyl (Cbz) protected amine derivative Abt4. The N-Boc groups were then removed by treatment with HCl, and the corresponding free amines where treated with N—,N'-Boc triflylguanadine to afford tri-N, N'-Boc protected guanidine derivative Abt5. Global deprotected afforded Abt6 (where n is either 1 or 5), which was then conjugated to vancomycin hydrochloride to provide dendrimeric conjugate derivatives V-triguan-2C and V-triguan-6C.

Scheme 1 - Synthesis of Exemplary dendrimeric conjugate

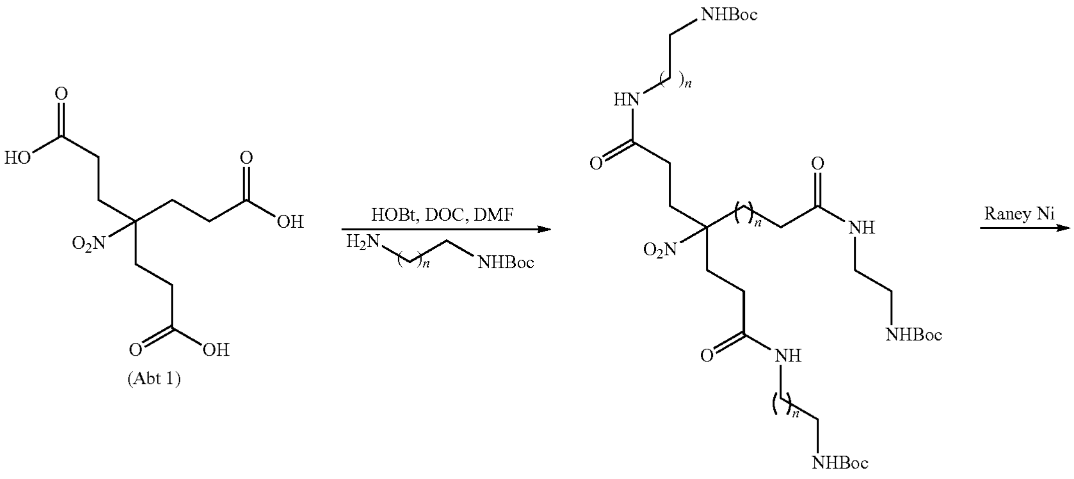

(Abt 1)

(Abt 2)

-continued
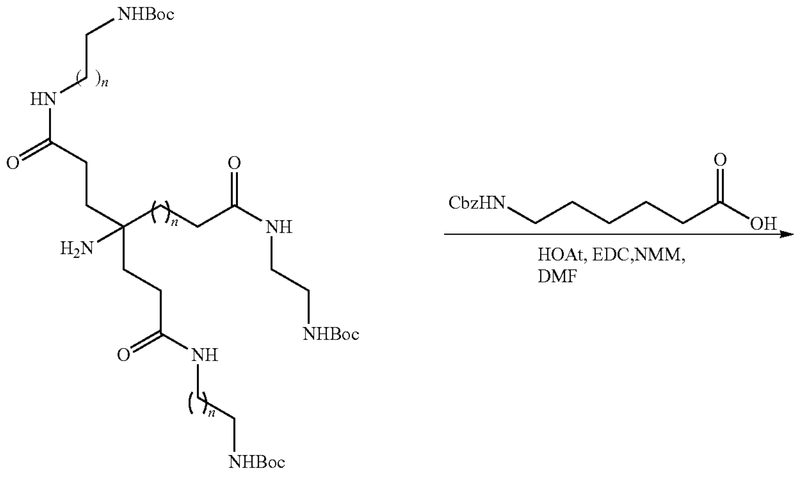
(Abt3)
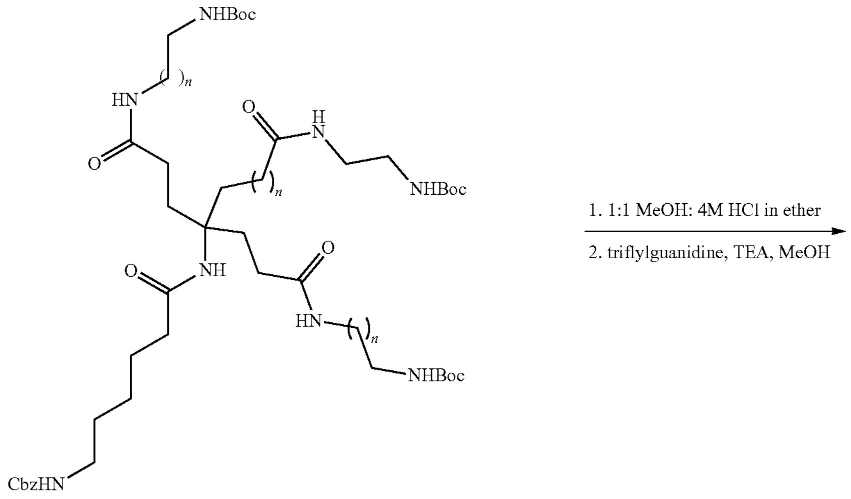
(Abt 4)
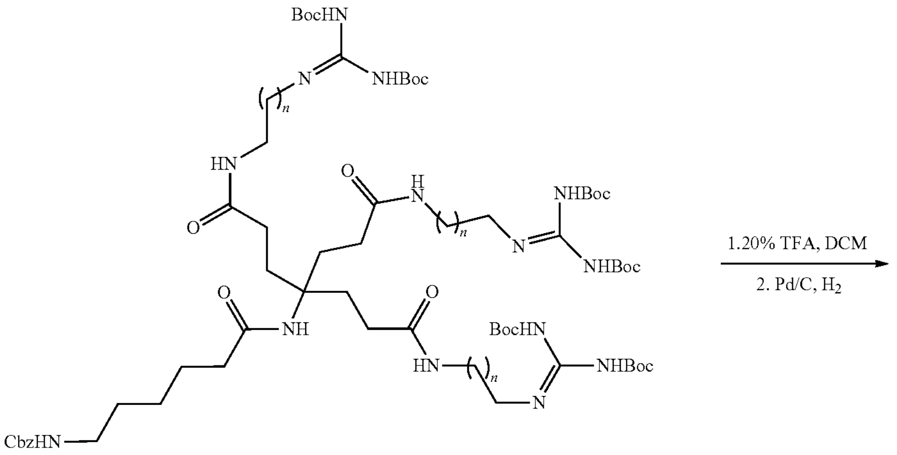
(Abt5)

-continued

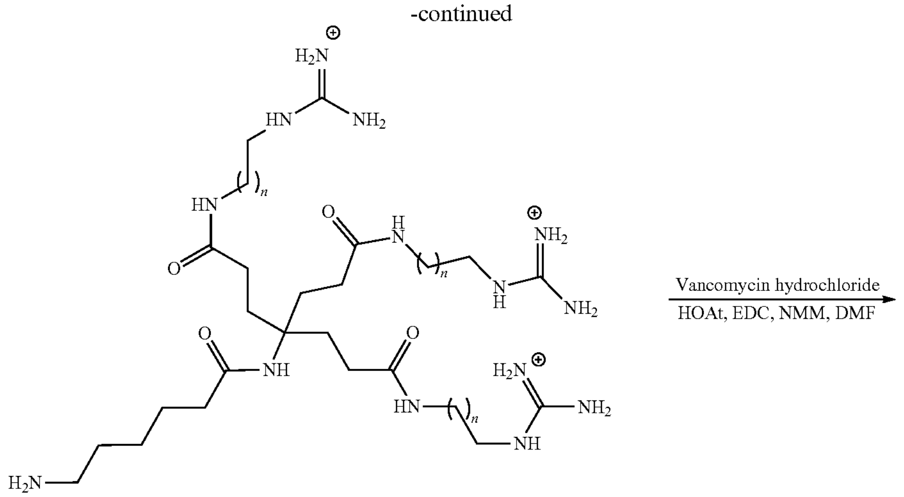

(Abt6)

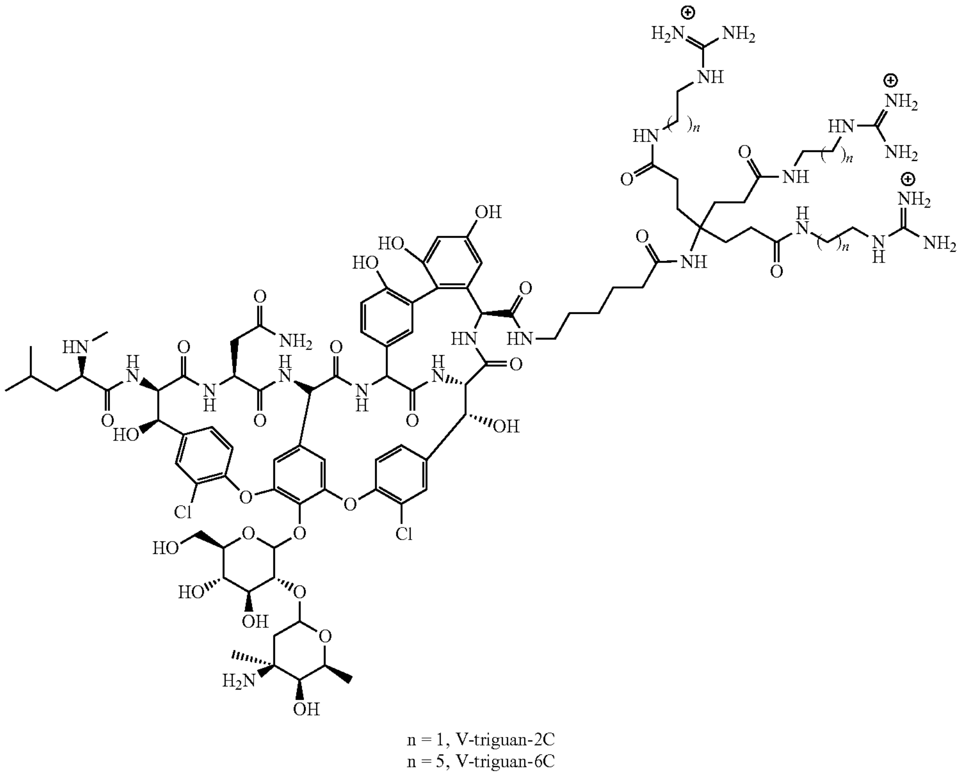

n = 1, V-triguan-2C
n = 5, V-triguan-6C

Scheme 1—Synthesis of Exemplary Dendrimeric Conjugate

Synthesis of Abt2: Abt1 (1 equiv.), HOBt (4 equiv.) and DCC (4 equiv.) were introduced in appropriate masses into an oven dried vial. DMF was added into the vial under nitrogen. The reaction mixture was stirred for 1.5 hour and N-boc diamine (4 equiv.) was added dropwise. The reaction mixture was then stirred overnight under nitrogen and the reaction was subsequently quenched by concentration in vacuo. The crude reaction mixture was then washed with water, 1N HCl aqueous solution, saturated sodium bicarbonate aqueous solution and finally saturated sodium chloride solution. After concentration in vacuo, the crude product was purified with 5% MeOH:DCM to afford a pale yellow oil in 60-99% yield.

Synthesis of Abt3: Abt2 (1 equiv.) was introduced into an oven dried round bottom flask with a stir bar in it. Ethanol was added into the round bottom flask to fully dissolve Abt2. A scoop of Raney nickel was quickly added into the round bottom flask, which was subsequently sealed, purged with hydrogen for 5 min and left under hydrogen. The reaction mixture was stirred overnight and then filtered through Celite. The celite was rinsed with MeOH and DCM, and the filtrate was concentrated in vacuo to yield the desired product in 78~90% yield.

Synthesis of Abt4: Into a flame-dried vial was added Cbz-Ahx-OH (1.5 equiv.), HOAt (5.4 equiv.), EDC (5.1 equiv.) and anhydrous DMF under nitrogen. Abt3(1 equiv.) was dissolved with dry DMF and added dropwise to reaction mixture. DIPEA (10% v/v) was then added dropwise to the reaction system via syringe. The color of the solution immediately turned bright yellow upon the addition of DIPEA. Reaction was stirred at room temperature for approximately 48 hours and quenched by concentration in vacuo. The crude reaction mixture was then washed with water, 1N HCl aqueous solution, saturate sodium bicarbonate aqueous solution and finally saturated sodium chloride solution. After concentration in vacuo, the crude product was purified with 5% MeOH:DCM to afford a clear oil in 52-65% yield.

Synthesis of Abt5: Abt4 (1 equiv.) was introduced into an oven-dried vial with a stir bar in it. 1:1 mixture of methanol and 2 M HCl in diethyl ether was add to the vial. The solution gradually turned from clear to opaque over the course of 2 hours, after which the reaction mixture was concentrated and left under high vacuum overnight. The obtained solid was dissolved in dry methanol followed by the sequent addition of triethylamine (20 equiv.) and N,N'-Boc triflylguanadine (3.9 equiv). The reaction was stirred overnight and later concentrated in vacuo. The crude product afforded was purified with 5% MeOH:DCM to afford a pale yellow oil in 59% yield.

Synthesis of Abt6: Abt5 (1 equiv.) was introduced into an oven-dried vial with a stir bar in it. Anhydrous DCM was added to the vial and the reaction mixture was stirred until Abt5 was fully dissolved. TFA (20% v/v) was added dropwise and the reaction mixture was stirred for two hours, during which the solution gradually turned pale brown. The reaction mixture was concentrated and left under high vacuum overnight. The obtained solid was then resuspended in dry MeOH, followed by the addition of Pd/C (10% wt/wt) into the vial. The vial was then purged with hydrogen for 5 minutes, left under hydrogen balloon, and stirred overnight. Next day the solution was filtered through Celite to remove Pd/C. The Celite was rinsed with MeOH and DCM, and the filtrate was concentrated in vacuo. The crude product was purified by semiprep-HPLC (0~30~100~100% $CH_3CN$/$H_2O$, 35 minutes). The appropriate fractions were lyophilized and the product was isolated as a white solid (90% yield).

Synthesis of V-triguan-2C/6C: Into a flame-dried vial under nitrogen environment was added vancomycin hydrochloride (1.5 equiv.), HOAt (5.4 equiv.), EDC (5.1 equiv.) and DMF. Abt6 (1 equiv.) was dissolved with DMF and added to the reaction mixture. DIPEA (10% v/v) was then added dropwise to the reaction system via syringe. The color of the solution immediately turned from pale yellow to bright yellow upon the addition of DIPEA. Reaction was stirred at room temperature for approximately 48 hours after LC-MS confirmed the presence of the product. Water was subsequently added to the reaction mixture and then lyophilized overnight. The crude product was purified by semi-prep-HPLC (5~70~100~100% CH3CN/H2O, 35 minutes). The appropriate fractions were lyophilized and the product was isolated as a white solid (12.6% yield).

Example 2

Antibacterial Activity Assays with Assay Conditions Listed

Methods—Determination of MICs: MICs for *S. aureus, E. faecium, E. coli, P aeruginosa, A. baumannii, K. pneumoniae* were determined using broth microdilution in accordance with CLSI methods (Wiegand, I.; Hilpert, K.; Hancock, R. E. W. Agar and Broth Dilution Methods to Determine the Minimal Inhibitory Concentration (MIC) of Antimicrobial Substances. Nat. Protoc. 2008, 3, 163-175). One day prior to each MIC experiment, bacterial strains were streaked for single colonies on TSA plates from frozen glycerol stocks stored at −80° C. Three to five colonies from each plate were harvested with a disposable inoculating loop and resuspended in 500 μL of PBS to create a bacterial suspension. Alternatively, a single colony of the appropriate bacterial strain was added to 4 mL TSB for overnight growth at 37° C. with 200 rpm shaking to create a stationary phase bacterial suspension. The suspension was diluted in PBS to an $OD_{600}$ of 0.1 (~$1\times10^8$ CFU/ml), and the OD 0.1 suspension was diluted 1:100 in Mueller Hinton broth (MHB, Difco 257530) just prior to inoculating the 96-well polypropylene treatment plate (Costar 3879). A 50 μL portion of inoculum was added to a treatment plate containing 2-fold serial dilutions of compound in MHB (50 μL of treatment/well) to lend a final total volume of 100 μL/well and a final inoculum density of ~$5\times10^5$ CFU/ml. The completed assay plate was sealed with Parafilm, placed in a lidded plastic tray lined with moistened paper towels, and incubated at 37° C. for approximately 20 hours. The MIC was read as the lowest treatment concentration where no bacterial growth occurred, as determined by $OD_{600}$ measurements on a microplate reader. If a different plate or media type was used for a particular test, this is noted below the respective table.

MICs for *C. glutamicum* and the mycobacteria, *M. smegmatis* and *M. abscessus*, were determined as follows. A suspension of stationary phase culture was adjusted with PBS to approximately $10^8$ CFU/mL and diluted 1:100 in nutrient media just prior to inoculating 96-well polystyrene treatment plates (Costar 3370). Nutrient media was Mueller Hinton Broth for *C. glutamicum* and Middlebrook media (Middlebrook 7H9 Broth with 0.2% glycerol and 10% OADC supplement, Difco, BD) for mycobacteria. A 50 μL portion of inoculum was added to a treatment plate containing 2-fold serial dilutions of compounds in the same media (50 μL of treatment/well) to lend a final total volume of 100 μL/well and a final inoculum density of ~$5\times10^5$ CFU/ml. The completed assay plate was sealed with Parafilm, placed in a lidded plastic tray lined with moistened paper towels, and incubated at 37° C. for around 22 h (*C. glutamicum*), 42-44 h (*M. smegmatis*) or 46-48 hours (*M. abscessus*). Then, 15 μL of 0.02% resazurin solution was added to each well and the plates were incubated further for 1 hour (*C. glutamicum*), 6 hours (*M. smegmatis*) or 20 hours (*M. abscessus*). The MIC was identified as the lowest treatment concentration of drug that prevented color change of resazurin from blue to pink/violet, as determined by measuring fluorescence in a black microtiter plate with excitation at 570 nm and emission at 615 nm on a Molecular Devices M5 microplate reader.

Table 1: shows Vancomycin-Dendrimer MIC Evaluation. Vancomycin-dendrimer conjugates are effective against Gram-positive bacteria, including VRE, and Gram-negative bacteria, including *E. coli* and *P. aeruginosa*. Vancomycin-dendrimer conjugates are also effective against mycobacteria, including *M. smegmatis* and *M. abscessus*. Vancomycin-dendrimer conjugates are also effective against Corynebacterium glutamicum, which is used as a surrogate in infection models for *M. tuberculosis*. The dendrimer molecules alone do not exhibit antibacterial activity. When dendrimers are added non-covalently with vancomycin, they do not increase efficacy against in this MIC assay for planktonically grown cells.

TABLE 1

Vancomycin-Dendrimer MIC Evaluation against Gram-positive *S. aureus* and *E. faecium*

| MIC (μM) | Vancomycin | V-triguan-6C | V-triguan-2C | V + $NH_2$-triguan-6C | $NH_2$-triguan-6C |
|---|---|---|---|---|---|
| *S. aureus* ATCC 29213 | 0.5-1 | 0.5-1 | 0.5 | 1 | >128 |
| *S. aureus* USA400 (MRSA) | 1 | 0.5-1 | 1 | 1 | >128 |
| *E. faecium* ATCC 51559 (VRE) | 512 | 8-16 | 16-32 | >64 | >128 |

TABLE 2

Vancomycin-Dendrimer MIC Evaluation against Mycobacteria and *Corynebacterium glutamicum*

| MIC (μM) | Vancomycin | V-triguan-6C | V-triguan-2C |
|---|---|---|---|
| *M. smegmatis* | 8-16 | 1 | 1 |
| *M. abscessus* | 64 | 16 | >16 |
| *C. glutamicum* | 0.25 | 0.031 | 0.031 |

TABLE 3

Vancomycin-Dendrimer MIC Evaluation against Gram-negative bacteria

| MIC (μM) | Vancomycin | V-triguan-6C | V-triguan-2C | V + $NH_2$-triguan-6C | $NH_2$-triguan-6C |
|---|---|---|---|---|---|
| *E. coli* ATCC 25922 | 128 | 8-16 | 8 | 64 to >64 | >128 |
| *E. coli* UTI89 | 128 | 8 | 8 | >64 | >128 |
| *E. coli* NCTC 13846 (colistin-resistant) | 64-128 | 2 | 4 | 32 | >128 |
| *E. coli* BW25113 | 128 | 4-8 | 4-8 | >64 | 128 |
| *E. coli* BW25113ΔtolC | 128-256 | 2 | 2-4 | 64 | 64-128 |
| *A. baumannii* ATCC 19606 | 128 | 8 | 32 | >64 | >128 |
| *K. pneumoniae* BAA-2146 | >256 | 32-64 | >128 | >64 | >128 |
| *P. aeruginosa* PA14 | >256 | 32-64 | 64 | >64 | >128 |

Table 4: shows the evaluation of non-covalent dendrimer and antibiotic mixtures against *S. aureus* (ATCC 29213). No enhancement of antibiotic MIC values were observed for antimicrobial killing of exponentially growing cells.

TABLE 4

Evaluation of non-covalent dendrimer and antibiotic mixtures against *S. aureus* (ATCC 29213)

| MIC (μM) | Target | Literature MIC | Antibiotic Alone | Antibiotic +NO2-triamine-2C | Antibiotic +NO2-triamine-6C | Antibiotic +NH2-triguan-6C |
|---|---|---|---|---|---|---|
| Ampicillin | Cell wall | 1.4 | 2 | 4 | 4 | 4 |
| Meropenem | Cell wall | 0.08-0.65 | 0.125 | 0.125 | 0.125 | 0.125 |
| Penicillin G | Cell wall | 0.084-5.6 | 2 | 4 | 4 | 2 |
| Vancomycin | Cell wall | 0.34-1.4 | 0.5-1 | 1 | 0.5-1 | 1 |
| Ciprofloxacin | DNA rep. | 0.4-1.5 | 1 | 0.5 | 0.5 | 1 |
| Daptomycin[B] | Cell membrane | 0.077-0.62 | 0.5 | 0.5 | 0.5 | 0.5 |

TABLE 4-continued

Evaluation of non-covalent dendrimer and antibiotic mixtures against *S. aureus* (ATCC 29213)

| MIC (μM) | Target | Literature MIC | Antibiotic Alone | Antibiotic +NO2-triamine-2C | Antibiotic +NO2-triamine-6C | Antibiotic +NH2-triguan-6C |
|---|---|---|---|---|---|---|
| Nitrofurantoin | Intracellular components | 33.6-134 | 128 | 256 | 256 | 128 |
| Rifampicin | RNA syn. | 0.005-0.019 | 0.016 | 0.016 | 0.016 | 0.016 |
| Tetracycline[A] | Protein syn. | 0.28-2.25 | 2 | 2 | 2 | 2 |
| Azithromycin | Protein syn. | 0.64-2.5 | 2 | 2 | 2 | 2 |
| Chloramphenicol | Protein syn. | 6-50 | 32 | 32 | 32 | 32 |
| Gentamicin | Protein syn. | 0.26-2.1 | 0.5 | 0.5 | 1 | 0.5 |

96-well assay plates: Costar 3879, polypropylene (unless noted by superscript).
Nutrient Medium: Mueller Hinton Broth (unless noted by superscript).
[A]Assay performed with cation-adjusted MHB2 and a polystyrene microwell plate (Costar 3370) as recommended for standard antibiotic testing of non-cationic peptide compounds.
[B]Assay performed with cation-adjusted MHB2 supplemented with 50 g/L $Ca^{2+}$ as specified for daptomycin.

Table 5 shows evaluation of non-covalent dendrimer/antibiotic mixtures against *E. coli* (ATCC 25922). No enhancement of MIC was observed.

TABLE 5

Evaluation of non-covalent dendrimer/antibiotic mixtures against *E. coli* (ATCC 25922)

| MIC (μM) | Target | Literature MIC | Antibiotic Alone | Antibiotic +NO2-triamine-2C | Antibiotic +NO2-triamine-6C | Antibiotic +NH2-triguan-6C |
|---|---|---|---|---|---|---|
| Ampicillin | Cell wall | 5-22 | 16 | 16 | 16 | 16 |
| Chloramphenicol | Protein syn. | 6-25 | 16 | 16 | 16 | 16 |

TABLE 6

Vancomycin-Dendrimer Minimum Bacterial Eradication Concentration (MBEC) assay with *S. aureus* USA400 (MRSA).

| MBEC (μM) | Vancomycin | V-triguan-6C | V-triguan-2C |
|---|---|---|---|
| *S. aureus* MW2 | >512 | 4 | 16 |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:
1. A compound selected from the following structures:
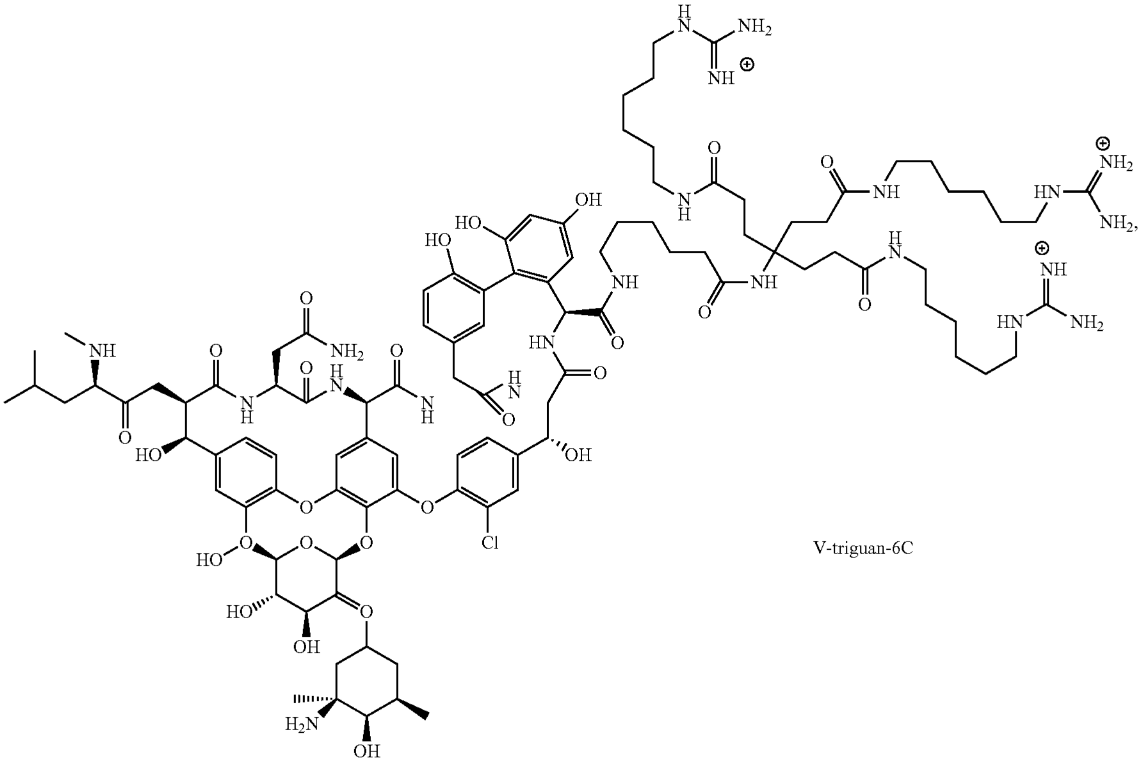
and
V-triguan-6C
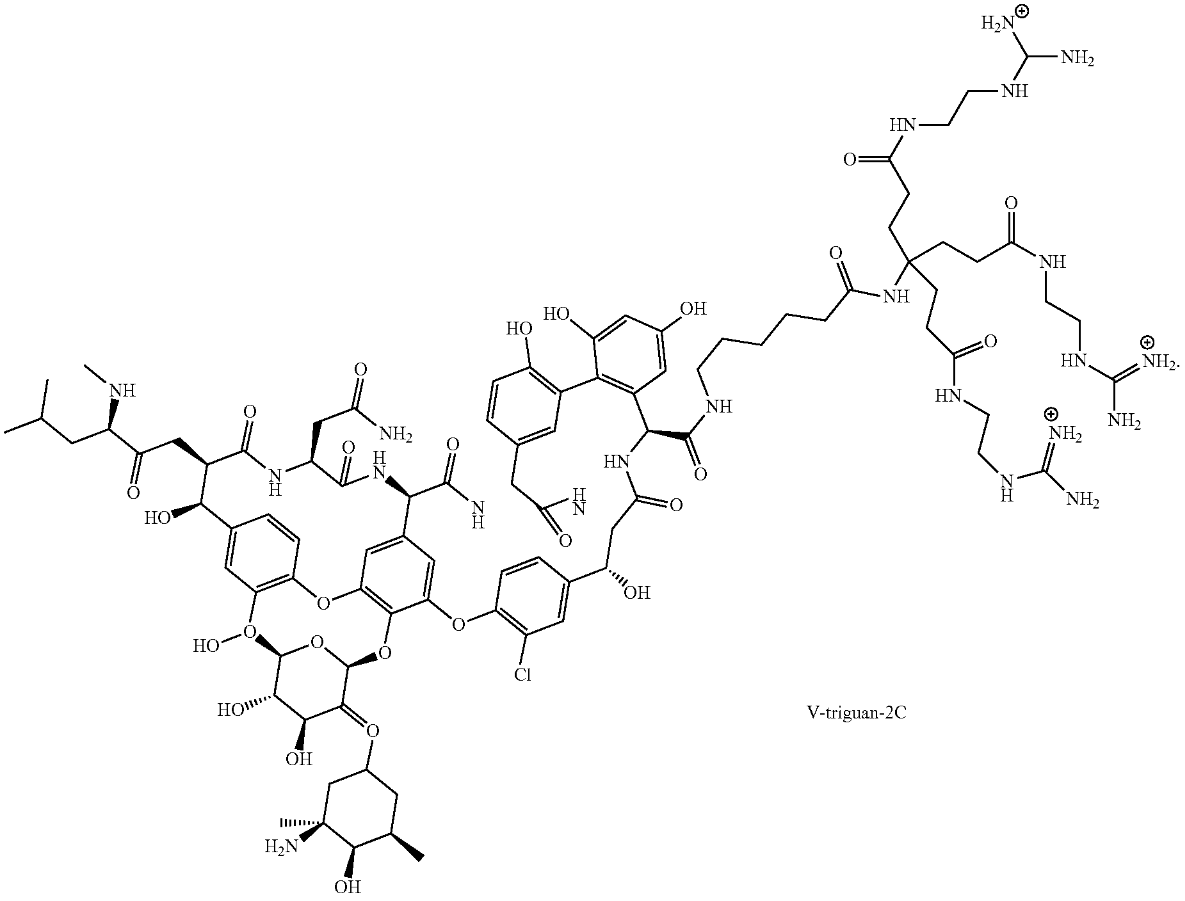
V-triguan-2C

2. A pharmaceutical composition comprising the compound of claim 1, and a pharmaceutically acceptable excipient.

* * * * *